(12) United States Patent
Shuttleworth et al.

(10) Patent No.: US 11,779,586 B2
(45) Date of Patent: *Oct. 10, 2023

(54) COMPOUNDS COMPRISING TRICYCLIC HETEROCYCLIC COMPOUNDS

(71) Applicant: Convalife (Shanghai) Co. Limited, Shanghai (CN)

(72) Inventors: Stephen Joseph Shuttleworth, Oxfordshire (GB); Elisabeth Ann Bone, Oxfordshire (GB); Franck Alexandre Silva, Oxfordshire (GB); Alexander Richard Liam Cecil, Oxfordshire (GB)

(73) Assignee: Convalife (Shanghai) Co. Limited, Shanghai (CN)

( * ) Notice: Subject to any disclaimer, the term of this patent is extended or adjusted under 35 U.S.C. 154(b) by 102 days.

This patent is subject to a terminal disclaimer.

(21) Appl. No.: 17/071,543

(22) Filed: Oct. 15, 2020

(65) Prior Publication Data
US 2021/0275537 A1    Sep. 9, 2021

Related U.S. Application Data

(63) Continuation of application No. 15/753,359, filed as application No. PCT/GB2016/052577 on Aug. 19, 2016, now abandoned.

(30) Foreign Application Priority Data

Aug. 19, 2015 (GB) ...................................... 1514758

(51) Int. Cl.
*A61K 31/5377* (2006.01)
*A61K 9/20* (2006.01)
*A61K 31/5386* (2006.01)

(52) U.S. Cl.
CPC ........ *A61K 31/5377* (2013.01); *A61K 9/2018* (2013.01); *A61K 9/2027* (2013.01);
(Continued)

(58) Field of Classification Search
CPC .............. A61K 31/5377; A61K 9/2018; A61K 9/2027; A61K 9/2054; A61K 9/2095;
(Continued)

(56) References Cited

U.S. PATENT DOCUMENTS 3,491,092 A    1/1970    Grigat et al.
4,017,500 A    4/1977    Mayer et al.
(Continued)

FOREIGN PATENT DOCUMENTS

EP    1277738 A1    1/2003
EP    1724267 A1    11/2006
(Continued)

OTHER PUBLICATIONS

Alvarez-Rua et al., "Multiple hydrogen bonds and tautomerism in naphthyridine derivatives", New J. Chem. 28, 2004, 700-707.
(Continued)

*Primary Examiner* — Kortney L. Klinkel
*Assistant Examiner* — Padmaja S Rao
(74) *Attorney, Agent, or Firm* — DLA PIPER LLP (US)

(57) ABSTRACT

The invention relates to a pharmaceutical composition comprising a compound of formula I or a pharmaceutically acceptable salt thereof, and at least one pharmaceutical excipient selected from the group consisting of fillers, binders, disintegrants, glidants and lubricants, wherein the compound according to formula I is represented by:
(Continued)

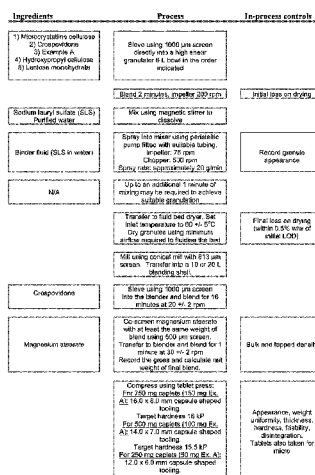

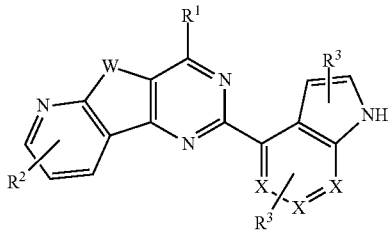

(I)

12 Claims, 1 Drawing Sheet

(52) U.S. Cl.
CPC .......... *A61K 9/2054* (2013.01); *A61K 9/2095* (2013.01); *A61K 31/5386* (2013.01)

(58) Field of Classification Search
CPC .............. A61K 31/5386; A61K 31/519; A61K 9/2027; A61P 19/02; A61P 29/00; A61P 35/00; A61P 35/02; A61P 37/02; A61P 37/06

See application file for complete search history.

(56) References Cited

U.S. PATENT DOCUMENTS

| | | | |
|---|---|---|---|
| 5,703,075 | A | 12/1997 | Gammill et al. |
| 7,182,958 | B1 | 2/2007 | Oren et al. |
| 7,361,662 | B2 | 4/2008 | Rault et al. |
| 8,242,116 | B2 | 8/2012 | Alexander et al. |
| 8,338,592 | B2 | 12/2012 | Alexander et al. |
| 8,710,054 | B2 | 4/2014 | Alexander et al. |
| 8,921,361 | B2 | 12/2014 | Cmiljanovic et al. |
| 8,981,087 | B2 | 3/2015 | Shuttleworth et al. |
| 9,200,007 | B2 | 12/2015 | Shuttleworth et al. |
| 9,266,879 | B2 | 2/2016 | Shuttleworth et al. |
| 9,580,442 | B2 | 2/2017 | Shuttleworth et al. |
| 9,663,487 | B2 | 5/2017 | Shuttleworth et al. |
| 9,868,749 | B2 | 1/2018 | Alexander et al. |
| 9,890,174 | B2 | 2/2018 | Alexander et al. |
| 9,932,343 | B2 | 4/2018 | Alexander et al. |
| 9,938,290 | B2 | 4/2018 | Shuttleworth et al. |
| 9,981,987 | B2 | 5/2018 | Shuttleworth et al. |
| 10,035,785 | B2 | 7/2018 | Shuttleworth et al. |
| 10,087,179 | B2 | 10/2018 | Alexander et al. |
| 10,377,764 | B2 | 8/2019 | Shuttleworth et al. |
| 10,442,815 | B2 | 10/2019 | Shuttleworth et al. |
| 10,501,478 | B2 | 12/2019 | Shuttleworth et al. |
| 10,513,530 | B2 | 12/2019 | Shuttleworth et al. |
| 10,668,077 | B2 | 6/2020 | Shuttleworth et al. |
| 11,291,669 | B2 | 4/2022 | Shuttleworth et al. |
| 2002/0151544 | A1 | 10/2002 | Hayakawa et al. |
| 2007/0135466 | A1 | 6/2007 | Ledeboer et al. |
| 2011/0201608 | A1 | 8/2011 | Hoffmann et al. |
| 2014/0163033 | A1 | 6/2014 | Bernal Anchuela et al. |
| 2015/0080395 | A1 | 3/2015 | Shuttleworth et al. |
| 2016/0113932 | A1 | 4/2016 | Stern et al. |
| 2018/0235974 | A1 | 8/2018 | Shuttleworth et al. |
| 2018/0243317 | A1 | 8/2018 | Shuttleworth et al. |
| 2020/0354378 | A1 | 11/2020 | Shuttleworth et al. |
| 2022/0041624 | A1 | 2/2022 | Shuttleworth et al. |
| 2022/0273667 | A1 | 9/2022 | Ward |

FOREIGN PATENT DOCUMENTS

| | | | |
|---|---|---|---|
| GB | 1402431 | A | 8/1975 |
| WO | 2001083456 | A1 | 8/2001 |
| WO | 2002002551 | A1 | 1/2002 |
| WO | 2002085400 | A1 | 10/2002 |
| WO | 2004006846 | A2 | 1/2004 |
| WO | 2004043956 | A1 | 5/2004 |
| WO | 2005117889 | A1 | 12/2005 |
| WO | 2006046035 | A1 | 5/2006 |
| WO | 2006127587 | A1 | 11/2006 |
| WO | 2007084667 | A2 | 7/2007 |
| WO | 2007122410 | A1 | 11/2007 |
| WO | 2007127183 | A1 | 11/2007 |
| WO | 2008064018 | A1 | 5/2008 |
| WO | 2008076447 | A2 | 6/2008 |
| WO | 2008094992 | A2 | 8/2008 |
| WO | 2008121257 | A1 | 10/2008 |
| WO | 2008145688 | A2 | 12/2008 |
| WO | 2008150827 | A1 | 12/2008 |
| WO | 2010015520 | A1 | 2/2010 |
| WO | 2010037765 | A2 | 4/2010 |
| WO | 2010052569 | A2 | 5/2010 |
| WO | 2011012883 | A1 | 2/2011 |
| WO | 2011021038 | A1 | 2/2011 |
| WO | 2011079231 | A1 | 6/2011 |
| WO | 2011135351 | A1 | 11/2011 |
| WO | 2013014448 | A1 | 1/2013 |
| WO | 2013017480 | A1 | 2/2013 |
| WO | 2013132270 | A1 | 9/2013 |
| WO | 2014081718 | A1 | 5/2014 |
| WO | 2014181137 | A1 | 11/2014 |
| WO | 2014210354 | A1 | 12/2014 |
| WO | 2015054099 | A1 | 4/2015 |
| WO | 2015054355 | A1 | 4/2015 |
| WO | 2015121657 | A1 | 8/2015 |
| WO | 2016075130 | A1 | 5/2016 |
| WO | 2017029514 | A1 | 2/2017 |
| WO | 2017029517 | A1 | 2/2017 |
| WO | 2017029518 | A1 | 2/2017 |
| WO | 2017029519 | A1 | 2/2017 |
| WO | 2017029521 | A1 | 2/2017 |
| WO | 2021001650 | A1 | 1/2021 |

OTHER PUBLICATIONS

Ameriks et al., "Small molecule inhibitors of phosphoinositide 3-kinase (PI3K) δ and γ", Current Topics in Medicinal Chemistry, 2009, 9(8):738-753.

Annex to Form PCT/ISA/206 Communication Relating to the Results of the Partial International Search for PCT/GB2016/052571 dated Nov. 9, 2016.

Bianchi et al., "Team work matters: dual inhibition puts non-Hodgkin lymphoma under siege", Clin. Cancer Res., 2014, 20(18):5863-5865.

Bodo et al., "The PI3K inhibitor GS-1101 (CAL-101) synergistically potentiates HDAC-induced proliferation inhibition and apoptosis through the activation of JNK in lymphoma cells", Blood, 2012, 120(21):3714.

Brachmann et al., "PI3K and mTOR inhibitors—a new generation of targeted anticancer agents", Current Opinion in Cell Biology, 2009, 21: 194-198.

CAS Registry Nos. 1214438-02-4 and 1214393-37-9 (Mar. 25, 2010).

Cohen et al., "The development and therapeutic potential of protein kinase inhibitors", Current Opinion in Chemical Biology, 1999, 3:459-465.

Database Chemcats [Online], Chemical Abstracts Service, Apr. 22, 2011.

European Search Report for EP 18202398.6 dated Feb. 15, 2019.

Fabbro et al., "Protein kinases as targets for anticancer agents: from inhibitors to useful drugs", Pharmacology & Therapeutics, 93 (2002): 79-98.

Golub et al., "Molecular classification of cancer: class discovery and class prediction by gene expression monitoring", Science, Oct. 15, 1999, 286: 531-537.

Hayakawa et al., "Synthesis and biological evaluation of pyrido[3′,2′:4,5]furo[3,2-d]pyrimidine derivatives as novel PI3K p110α inhibitors", Bioorganic and Medicinal Chemistry Letters, Feb. 15, 2007, 17(9):2438-2442.

(56) References Cited

OTHER PUBLICATIONS

Hollebecque et al., "A phase Ib trial of LY2584702 tosylate, a p70 S6 inhibitor, in combination with erlotinib or everolimus in patients with solid tumours," Eur. J Cancer, 2014, 50(5):876-884.
International Preliminary Report on Patentability for PCT/GB2010/051221 dated Jan. 31, 2012.
International Preliminary Report on Patentability for PCT/GB2010/051370 dated Feb. 21, 2012.
International Preliminary Report on Patentability for PCT/GB2011/050824 dated Nov. 6, 2012.
International Preliminary Report on Patentability for PCT/GB2013/050583 dated Sep. 9, 2014.
International Preliminary Report on Patentability for PCT/GB2015/050396 dated Aug. 16, 2016.
International Search Report and Written Opinion for PCT/GB2010/051221 dated Oct. 7, 2010.
International Search Report and Written Opinion for PCT/GB2010/051370 dated Nov. 9, 2010.
International Search Report and Written Opinion for PCT/GB2011/050824 dated Jul. 12, 2011.
International Search Report and Written Opinion for PCT/GB2013/050583 dated May 6, 2013.
International Search Report and Written Opinion for PCT/GB2015/050396 dated Mar. 25, 2015.
International Search Report and Written Opinion for PCT/GB2016/052571 dated Feb. 23, 2017.
International Search Report and Written Opinion for PCT/GB2016/052575 dated Nov. 9, 2016.
International Search Report and Written Opinion for PCT/GB2016/052577 dated Nov. 9, 2016.
International Search Report and Written Opinion for PCT/GB2016/052578 dated Oct. 25, 2016.
International Search Report and Written Opinion for PCT/GB2016/052581 dated Oct. 24, 2016.
International Search Report and Written Opinion for PCT/GB2020/051582 dated Oct. 8, 2020.
Kovalskiy et al., "Synthesis of 7-(3-piperidyl)[1,6]naphthyridine and 7-(4-piperidyl)[1,6]naphthyridine", Chemistry of Heterocyclic Compounds, Nov. 24, 2009, 45(9):1053-1057.
Lin et al., "Dual targeting of glioblastoma multiforme with a proteasome inhibitor (Velcade) and a phosphatidylinositol 3-kinase inhibitor (ZSTK474)", Int. J. Oncol., 2014, 44(2):557-562.
Liu et al., "mTOR mediated anti-cancer drug discovery", Drug Discovery Today: Therapeutic Strategies, 2009, 6 (2):47-55.
Mass, "The HER receptor family: a rich target for therapeutic development", Int. J. Radiation Oncology Bio. Phys., 2004, 58(3):932-940.
Meredith et al., "Identification of orally available naphthyridine protein kinase D inhibitors", Journal of Medicinal Chemistry, Aug. 12, 2010, 53(15):5400-5421.
Saifuddin et al., "Water-accelerated cationic TT-(7-endo) cyclisation: application to indole-based peri-annulated polyheterocycles", European Journal of Organic Chemistry, 2010, 26, 5108-5117.
Schröder et al., "Arzneimittel Chemie Passage," Arzneimittelchemie Grundlagen Nerven, Muskeln und Gewebe [Pharmaceutical Chemistry I: Basic, Nerves, Muscles and Tissues], 1st Ed., 1976, Thieme Georg Verla, pp. 30-33 and Table 8 (XP002186820).
Shuttleworth et al., "Progress in the preclinical discovery and clinical development of Class I and dual Class I/IV phosphoinositide 3-kinase (PI3K) inhibitors", Current Medicinal Chemistry, 2011, 18: 2686-2714.
Singh et al., "Novel cAMP PDE III inhibitors: 1,6-naphthyridin-2(1H)-ones", J. Med. Chem., American Chemical Society, Jan. 1, 1992, 35(26): 4858-4865.
Somei et al., "Boronation-thallation, a new approach to the synthesis of indoles having aryl and/or a heteroaryl substituent at the 4-position", Chem. Pharm. Bull. 1986, 34, 3971-3973.
Tao et al., "Combined treatment of BTK and PI3K inhibitors synergistically disrupts BCR-signaling, overcomes microenvironment-mediated survival and drug resistance in mantle cell lymphoma", Proceedings of the 104th Annual Meeting of the American Association for Cancer Research, Apr. 6-10, 2013, AACR Abstract #4944 (2 pages) (Abstract).
Verheijen et al., "Phosphatidylinositol 3-kinase (PI3K) inhibitors as anticancer drugs", Drugs of the Future, 2007, 32 (6):537-547.
Yamada et al., "A novel HDAC inhibitor OBP-801 and a PI3K inhibitor LY294002 synergistically induce apoptosis via the suppression of survivin and XIAP in renal cell carcinoma", Int J. Oncol, 2013, 43(4): 1080-1086.
Zhao et al., "Discovery of novel Bruton's tyrosine kinase (BTK) inhibitors bearing a pyrrolo[2,3-d]pyrimidine scaffold", Bioorganic and Medicinal Chemistry, 2015, 23: 891-901.
Zhong et al., "Synergistic effects of concurrent blockade of PI3K and MEK pathways in pancreatic cancer preclinical models", PLoS One, Oct. 2013, 8(10):e77243.
Zhou et al., "Novel mutant-selective EGFR kinase inhibitors against EGFR T790M", Nature, Dec. 24, 2009, 462 (7276):1070-1074 [NIH Public Access Version].

| Ingredients | Process | In-process controls |
|---|---|---|
| 1) Microcrystalline cellulose<br>2) Crospovidone<br>3) Example A<br>4) Hydroxypropyl cellulose<br>5) Lactose monohydrate | Sieve using 1000 μm screen directly into a high shear granulator 6 L bowl in the order indicated | |
| | Blend 2 minutes, impeller 200 rpm | Initial loss on drying |
| Sodium lauryl sulfate (SLS)<br>Purified water | Mix using magnetic stirrer to dissolve | |
| Binder fluid (SLS in water) | Spray into mixer using peristaltic pump fitted with suitable tubing.<br>Impeller: 75 rpm<br>Chopper: 500 rpm<br>Spray rate: approximately 20 g/min | Record granule appearance |
| N/A | Up to an additional 1 minute of mixing may be required to achieve suitable granulation | |
| | Transfer to fluid bed dryer. Set inlet temperature to 60 +/- 5°C<br>Dry granules using minimum airflow required to fluidise the bed | Final loss on drying (within 0.5% w/w of initial LOD) |
| | Mill using conical mill with 813 μm screen. Transfer into a 10 or 20 L blending shell. | |
| Crospovidone | Sieve using 1000 μm screen into the blender and blend for 16 minutes at 20 +/- 2 rpm | |
| Magnesium stearate | Co-screen magnesium stearate with at least the same weight of blend using 500 μm screen.<br>Transfer to blender and blend for 1 minute at 30 +/- 2 rpm<br>Record the gross and calculate net weight of final blend. | Bulk and tapped density |
| | Compress using tablet press:<br>For 750 mg caplets (150 mg Ex. A): 16.0 x 8.0 mm capsule shaped tooling.<br>Target hardness 16 kP<br>For 500 mg caplets (100 mg Ex. A): 14.0 x 7.0 mm capsule shaped tooling.<br>Target hardness 15.5 kP<br>For 250 mg caplets (50 mg Ex. A): 12.0 x 6.0 mm capsule shaped tooling.<br>Target hardness 13 kP | Appearance, weight uniformity, thickness, hardness, friability, disintegration.<br>Tablets also taken for micro |

COMPOUNDS COMPRISING TRICYCLIC HETEROCYCLIC COMPOUNDS

FIELD OF THE INVENTION

The present invention relates to a formulation comprising compounds which act as inhibitors of the class IA phosphoinositide 3-kinase enzymes, PI3K-p110β and p110δ, for the treatment of cancer, immune and inflammatory diseases.

CROSS-REFERENCE TO RELATED APPLICATIONS

This application is a continuation of U.S. patent application Ser. No. 15/753,359, filed on Feb. 19, 2018, which is a national stage of International Patent Application No. PCT/GB2016/052577, filed on Aug. 19, 2016, which claims the benefit of and priority to Great Britain Patent Application No. 1514758.0, filed on Aug. 19, 2015, the contents of each of which are hereby incorporated by reference in their entirety.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110β and p110δ activity have important therapeutic potential in cancer and immune and inflammatory disorders.

In order to deliver the optimum amount of an active pharmaceutical ingredient to a patient, it is necessary to optimize physiochemical properties that include, but are not restricted to, solubility. Therefore, it is important to formulate such PI3K compounds into a form in which they can be readily dispensed to patients and/or used in clinical studies.

SUMMARY OF THE INVENTION

The present invention relates to a pharmaceutical composition comprising a disclosed compound, or a salt form thereof. Disclosed compositions may have increased activity and/or bioavailability over the compounds described in WO 2011/021038. The compound according to formula I, preferably in its salt form, will herein be referred to as the active pharmaceutical ingredient (API).

Therefore, the composition of the present invention comprises a compound of Formula I:

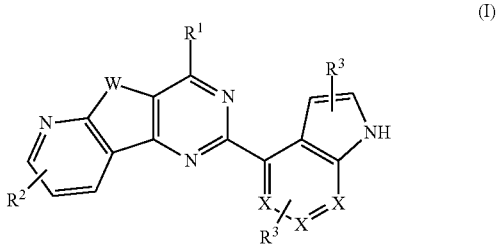

(I)

or a pharmaceutically acceptable salt thereof, wherein:
W is O, N—H, N—(C$_1$-C$_{10}$ alkyl) or S;
each X is selected independently for each occurrence from CH, CR$^3$, or N;
R$^1$ is a 5 to 7-membered saturated or unsaturated, optionally substituted heterocycle containing at least 1 heteroatom selected from N or O;
R$^2$ is L-Y;
each L is selected from the group consisting of a direct bond, C$_1$-C$_{10}$ alkylene, C$_2$-C$_{10}$ alkenylene and C$_2$-C$_{10}$ alkynylene;
Y is an optionally substituted fused, bridged or spirocyclic non-aromatic heterocycle containing up to 4 heteroatoms (for example, one, two, three or four heteroatoms) each independently selected from N or O, and comprising 5 to 12 carbon or heteroatoms in total; and
each R$^3$ is independently H, C$_1$-C$_{10}$ alkyl, halogen, fluoro C$_1$-C$_{10}$ alkyl, O—C$_1$-C$_{10}$ alkyl, —NH—C$_1$-C$_{10}$ alkyl, S—C$_1$-C$_{10}$ alkyl, O-fluoro C$_1$-C$_{10}$ alkyl, NH-acyl, NH—C(O)—NH—C$_1$-C$_{10}$ alkyl, C(O)—NH—C$_1$-C$_{10}$ alkyl, aryl or heteroaryl.

BRIEF DESCRIPTION OF FIGURES

FIG. 1 is a flow chart illustrating the process used for preparing a batch quantity of 1.2 kg of Example A in tablet form.

DESCRIPTION OF THE PREFERRED EMBODIMENTS

Definitions

As used herein, "alkyl" means a C$_1$-C$_{10}$ alkyl group, which can be linear or branched. Preferably, it is a C$_1$-C$_6$ alkyl moiety. More preferably, it is a C$_1$-C$_4$ alkyl moiety. Examples include methyl, ethyl, n-propyl and t-butyl. It may be divalent, e.g. propylene.

As used herein, "alkenyl" means a C$_2$-C$_{10}$ alkenyl group. Preferably, it is a C$_2$-C$_6$ alkenyl group. More preferably, it is a C$_2$-C$_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene.

As used herein, "alkynyl" is a C$_2$-C$_{10}$ alkynyl group which can be linear or branched. Preferably, it is a C$_2$-C$_4$ alkynyl group or moiety. It may be divalent.

Each of the C$_1$-C$_{10}$ alkyl, C$_2$-C$_{10}$ alkenyl and C$_2$-C$_{10}$ alkynyl groups may be optionally substituted with each other, i.e. C$_1$-C$_{10}$ alkyl optionally substituted with C$_2$-C$_{10}$ alkenyl. They may also be optionally substituted with aryl, cycloalkyl (preferably C$_3$-C$_{10}$), aryl or heteroaryl. They may also be substituted with halogen (e.g. F, Cl), NH$_2$, NO$_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, they may be substituted with $CF_3$, $CHF_2$, $CH_2CF_3$, $CH_2CHF_2$ or $CF_2CF_3$.

As used herein, the term "fluoro $C_1$-$C_{10}$ alkyl" means a $C_1$-$C_{10}$ alkyl substituted with one or more fluorine atoms. Preferably, one, two, three, four or five fluorine atoms. Examples of "fluoro $C_1$-$C_{10}$ alkyl" are $CF_3$, $CHF_2$, $CH_2F$, $CH_2CF_3$, $CH_2CHF_2$ or $CF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the term "heterocycle" or "heterocycloalkyl" is a mono- or divalent carbocyclic radical containing up to 4 heteroatoms selected from oxygen, nitrogen and sulfur. Preferably, it contains one or two heteroatoms. Preferably, at least one of the heteroatoms is nitrogen. It may be monocyclic or bicyclic. It is preferably saturated. Examples of heterocycles are piperidine, piperazine, thiomorpholine, morpholine, azetidine or oxetane. More preferably, the heterocycle is morpholine.

The heterocyclic ring may be mono- or di-unsaturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo (e.g. F), nitro, cyano, carboxy, $C_1$-$C_3$-haloalkyl (e.g. $CF_3$), $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In summary, each of the groups defined above, i.e., alkyl, alkenyl, alkynyl, aryl, heteroaryl, heterocycle, heterocycloalkyl, may be optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

It should be noted that —NH—$C_1$-$C_{10}$ alkyl, NH-acyl, NH—C(O)—NH—$C_1$-$C_{10}$ alkyl and C(O)—NH—$C_1$-$C_{10}$ alkyl can also be written as —N—$C_1$-$C_{10}$ alkyl, N-acyl, N—C(O)—N—$C_1$-$C_{10}$ alkyl and C(O)—N—$C_1$-$C_{10}$ alkyl.

As used herein, the above groups can be followed by the suffix-ene. This means that the group is divalent, i.e. a linker group.

As used herein, the term "fused" is intended to take its usual meaning within the art of organic chemistry. Fused systems, for example fused bicyclic systems, are those in which two rings share two and only two atoms.

As used herein, the term "bridged" is intended to take its usual meaning within the art of organic chemistry. Bridged compounds are compounds which contain interlocking rings. According to the invention, the atoms of the bridged non-aromatic group which form the bridgehead is either a tertiary carbon atom (when the remaining atom is hydrogen) or a quaternary carbon atom (when the remaining atom is not hydrogen). The bridge can be considered to be a chain of atoms (for example, alkyl) or a single atom (for example, O, S, N, C) connecting two bridgeheads.

As used herein, the term "spirocyclic" is intended to take its usual meaning within the art of organic chemistry. For example, a spirocyclic compound is a bicycle whose rings are attached through just one atom (known as a spiroatom). The rings may be different in size, or they may be the same size. Preferably, according to the invention, the two rings which are joined via the same atom are non-aromatic heterocycles, preferably heterocycloalkyls. For example, the spirocyclic non-aromatic group of Formula I may be a bicycle wherein both rings are heterocycloalkyl and are attached through the same atom, preferably a carbon atom.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

As described herein, enteric coatings or polymers used to coat pharmaceutical dosage forms include cellulose, vinyl, and acrylic derivatives. Enteric polymeric materials are primarily weak acids containing acidic functional groups, which are capable of ionization at elevated pH. The enteric coating may coat a core of a solid dosage form disclosed herein and controls the location in the digestive tract where the active agent contained in the solid dosage form's core is released and absorbed. In certain embodiments, the enteric coating is in the form of one or more components selected from the group including polymers, fatty acids, waxes, shellac, plastics, and plant fibers.

The enteric coating may comprise one or more of the following: acrylates and acrylate copolymers, including methacrylic acid/methacrylic acid methylester copolymer and methacrylic acid/ethyl acrylate copolymer; cellulose esters, including cellulose acetate phthalate, cellulose acetate trimellitate, and cellulose acetate succinate; hydroxypropyl methylcellulose phthalate; hydroxypropyl methylcellulose acetate succinate; polyvinyl derivatives, including polyvinyl acetate phthalate; and carboxymethyl ethyl cellulose. In some specific embodiments, the enteric coating includes one or more components sold under trade names, for example EMCOAT 120 N, MARCOAT 125, AQUACOAT CPD®, SEPIFILM™, AQUACOAT® ECD, METOLOSE®, SURETERIC®, and EUDRAGIT®. In certain preferred embodiments, the enteric coating may comprise colorants.

The enteric coating may further comprise a plasticizer. In some embodiments, the plasticizer will influence, i.e., increase or decrease, the rate of dissolution of the enteric coating. In some embodiments, the plasticizer may be lipophilic. In other embodiments, the plasticizer may be hydrophilic.

The plasticizer may comprise one or more of the group including cetanol, triacetin, citric acid esters such as triethyl citrate, phthalic acid esters such as diethyl phthalate and dibutyl phthalate, dibutyl succinate, propylene glycol, polyethylene glycol (PEG), and oils and glycerides such as fractional coconut oil.

The pharmaceutical composition may also comprise an antioxidant. Antioxidants are used to protect ingredients within the composition that are susceptible to oxidation by oxidising agents that are also included within the composition. Examples of antioxidants include water soluble antioxidants such as ascorbic acid, sodium sulfite, metabisulfite, sodium miosulfite, sodium formaldehyde, sulfoxylate, isoascorbic acid, isoascorbic acid, cysteine hydrochloride, 1,4-diazobicyclo-(2,2,2)-octane, and mixtures thereof. Examples of oil-soluble antioxidants include ascorbyl palmitate, butylated hydroxyanisole, butylated hydroxytoluene, potassium propyl gallate, octyl gallate, dodecyl gallate, phenyl-a-napthyl-amine, and tocopherols such as a-tocopherol.

Buffering agents may also be added to maintain an established pH of the composition. Examples of buffering agents include, but are not limited to, sodium citrate, calcium acetate, potassium metaphosphate, potassium phosphate monobasis and tartaric acid.

A bulking agent may also be added to the composition in order to provide bulk to the composition. Examples of bulking agents include, but are not limited to, PEGs, mannitol, dextran, cyclodextrins, trehalose, lactose, sucrose, polyvinyl pyrrolidone, glycine and derivatives thereof.

As used herein, disintegrant may be an intra or extra granular disintegrant. The disintegrant may be selected from the group consisting of starches, e.g. sodium carboxymethyl starch; clays; celluloses, e.g. low substitute hydroxy propyl cellulose; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. Preferably, the disintegrant used in the present invention comprises crospovidone or crosslinked sodium carboxymethyl cellulose, more preferably crospovidone.

As used herein, filler or diluent may be selected from the group consisting of microcrystalline cellulose, spray-dried lactose, mannitol DC, pregelatinised starch colloidal silicon dioxide, starches such as pregelatinized starch, calcium carbonate, confectioner sugar, compressible sugar, dextrates, dextrin, dextrose, lactose, powdered cellulose, sorbitol, sucrose, talc, calcium phosphate, calcium hydrogen phosphate dihydrate, ethyl cellulose, mannitol, magnesium carbonate, magnesium oxide, and sodium chloride.

As used herein, a binder may be selected from the group consisting of hydroxypropyl cellulose, hydroxypropyl methyl cellulose, sucrose, polysaccharides, lactose, starches, cellulose, microcrystalline cellulose, cellulose ethers, methyl cellulose, xylitol, sorbitol, and maltitol, gelatin, polyvinylpyrrolidone, polyethylene glycol, acacia, alginate, sodium alginate, alginic acid, candelilla wax, carnuba wax, corn starch, copolyvidone, povidone, a copolymer of 1-vinyl-2-pyrrolidone and vinyl acetate, and polyethylene oxide.

As disclosed herein, the formulation may further comprise a surfactant. Preferably, the surfactant is selected from the group consisting of non-ionic, anionic, cationic and zwitterionic surfactants and combinations thereof. These surfactants may include non-ionic surfactants such as fatty acid esters or amides or ether analogues, or hydrophilic derivatives thereof. Monoesters or diesters, or hydrophilic derivatives thereof; or mixtures thereof. Monoglycerides or diglycerides, or hydrophilic derivatives thereof; or mixtures thereof. Mixtures having enriched mono- or/and diglycerides, or hydrophilic derivatives thereof; maybe partially derivatized with a hydrophilic moiety; Monoesters or diesters or multiple-esters of other alcohols, polyols, saccharides or oligosaccharides or polysaccharides, oxyalkylene oligomers or polymers or block polymers; or hydrophilic derivatives thereof; the amide analogues thereof. Fatty acid derivatives of amines, polyamines, polyimines, aminoalcohols, aminosugars, hydroxyalkylamines, hydroxypolyimines, peptides, polypeptides; the ether analogues thereof. Surfactants can also be ionic or zwitterionic surfactants such as fatty acid salts, bile salts, sulfates, sulfonates, sulfosuccinates, carboxylates, lactylates, phospholipids and derivatives, quaternary ammonium salts, amine salts, polyethoxylated ammonium salts, or mixtures thereof.

The present invention includes the use of surfactants selected from sodium lauryl sulfate, sodium taurocholate, lecithin, lyso-lecithin, phosphatidyl glycerol, polyethylene glycol-phosphatidyl ethanolamine, cetyl trimethyl ammonium bromide, lauryl betaine, sucrose esters, polysorbates, sorbitan fatty acid esters, polyethylene glycosylated glycerides, PEGylated glycerides and combinations thereof. These non-ionic surfactants may include mixtures of monoglycerides, diglycerides, and triglycerides and monoesters and diesters of polyethylene glycol, polyethylene glycosylated almond glycerides, polyethylene glycosylated corn glycerides, polyethylene glycosylated caprylic/capric triglyceride, polysorbate 20, polysorbate 60, polysorbate 80, Polyoxyl 20 Cetostearyl Ether, Polyoxyl 10 Oleyl Ether and combinations thereof. Additionally suitable non-ionic surfactants include PEG stearate, PEG hydrogenated castor oil, PEG laurate, PEG apricot kernel oil esters, PEG caprylate, PEG caprate, PEG myristate, PEG palmitate, and PEG oleate and combinations thereof. Preferably, a surfactant used in the composition of the present invention is sodium lauryl sulfate or glyceryl monostearate. More preferably, the surfactant used in the composition of the present invention is sodium lauryl sulfate.

Such surfactants can be used in combination with other surfactants as co-surfactants. Suitable co-surfactants include surfactants selected from the above list having an HLB lower than 10.

As used herein, glidant may be selected from the group consisting of colloidal silicon dioxide, fumed silica, talc and magnesium carbonate.

As used herein, lubricants may be selected from the group consisting of minerals, such as talc and silica, and fats and fatty acids, such as vegetable stearin, magnesium stearate, stearic acid, calcium stearate, castor oil, glyceryl behenate, mineral oil, poloxamers, sodium lauryl sulfate, and sodium stearyl fumarate. The lubricant may also be selected from the group consisting of colloidal silica, magnesium trisilicate, starches, tribasic calcium phosphate, aluminium stearate, calcium stearate, magnesium carbonate, magnesium oxide, polyethylene glycol powdered cellulose and microcrystalline cellulose. Preferably, the lubricant used in the present invention comprises magnesium stearate.

A glidant is generally used in combination with a lubricant. They are used to promote powder flow by reducing interparticle friction and cohesion. Examples include, but are not limited to, fumed silica, talc, magnesium carbonate along with those listed above under those recited as lubricants.

A preservative may also be added to the composition according to the present invention. Preservatives are added in order to protect the composition from degradation and/or microbial contamination. Examples of preservatives include include liquipar oil, phenoxyethanol, methyl paraben, propyl paraben, butyl paraben, isopropyl paraben, isobutyl paraben, diazolidinyl urea, imidazolidinyl urea, diazolindyl urea, benzalkonium chloride, benzethonium chloride, phenol, and mixtures thereof (e.g., liquipar oil).

The amount of each excipient used herein may vary within ranges conventional in the art. However, preferred ranges are disclosed below.

The pharmaceutical compositions disclosed herein may be manufactured by any acceptable or art-recognized method including but not limited to: granulation of the core components to form a tablet mix prior to core formation using dry granulation, wet granulation, low shear wet granulation, high shear wet granulation, and fluid bed granulation; granule lubrication; compression of the tablet mix in a tablet press to form the core; coating of the core with an enteric coating using coating pans, spray coating, fluid-bed coating, dry coating, and the like. Preferably, the pharmaceutical composition and solid dosage form of the present invention is prepared using a wet granulation process. This process of tablet formation is well known to those skilled in the art.

Preferred Groups of the Invention
Formulation

Preferably the pharmaceutical composition of the invention is a composition suitable for oral administration, for example tablets and capsules.

Preferably, the active pharmaceutical ingredient, i.e. the compound according to Formula I, is present in an amount of from 0.1 to 50 wt %, more preferably 5 to 30 wt % based on the total weight of the composition.

Preferably, the composition comprises at least one filler in an amount of from 10 to 90 wt % based on the total weight of the composition, more preferably 10 to 64 wt % or 10 to 50 wt % based on the total weight of the composition.

Preferably, the composition comprises at least one binder in an amount of from 0.1 to 20 wt % based on the total weight of the composition, more preferably 1 to 20 wt % or 1 to 10 wt %.

Preferably, the composition comprises at least one disintegrant in an amount of from 1 to 20 wt % based in the total weight of the composition. More preferably, 1 to 10 wt %

Preferably, the composition comprises at least one lubricant or glidant in an amount of from 0.1 to 10 wt % based on the total weight of the composition. More preferably, the composition comprises at least one lubricant in an amount of from 0.5 to 5 wt %.

In an embodiment, the composition comprises:
1 to 50 wt % of a compound according to claim 1;
10 to 90 wt % of at least one filler;
0.1 to 20 wt % of at least one binder;
1 to 20 wt % of at least one disintegrant; and
0.1 to 10 wt % of at least one lubricant or glidant.

In an embodiment, the composition comprises:
0.1 to 50 wt % of a compound according to claim 1;
10 to 90 wt % of at least one filler;
0.1 to 20 wt % of at least one binder;
1 to 20 wt % of at least one disintegrant; and
0.2 to 10 wt % of at least one lubricant or glidant.

Preferably, the active pharmaceutical ingredient is in its salt form, preferably the succinate salt when in tablet form.

Preferably, when formulated as a tablet form, the composition does not contain any antioxidant or preservatives.

Preferably, the composition further comprises 0.1 to 5 wt % of at least one surfactant, more preferably 0.1 to 1 wt % of surfactant, based on the total weight of the composition.

Preferably, before the formulation is compressed into a solid dosage form, the particle/granule size is screened such that only particles/granules of less than 1000 µm are used, more preferably less than 500 µm. In other words, only particles/granules having a largest diameter size of less than 1000 µm, preferably less than 500 µm are used. This eliminates oversized particles that may interfere with rapid disintegration.

The pharmaceutical composition is preferably a solid dosage form (e.g. a powder, caplet, pill, tablet or capsule) and is preferably an oral solid dosage form. The composition is preferably in tablet form. Alternatively, the composition may be in capsule form. Any suitable tablet form can be used, as described in more detail below.

The following types of tablet forms are envisaged as part of the present invention:

Compressed Tablets—such tablets are formed by compression and contain no special coating. They are made from powdered, crystalline, or granular materials, alone or in combination with binders, disintegrants, controlled-release polymers, lubricants, diluents and sometimes colourants.

Film-Coated Tablets—such tablets are compressed tablets containing a sugar coating. Such coatings may be coloured and are beneficial in covering up drug compounds having an undesirable taste to the patient. Such coatings also protect materials in the tablet that can be sensitive to oxidation.

Enteric-Coated Tablets—these are compressed tablets coated with a substance that resists solution in the gastric fluid, but disintegrate in the intestine. Such enteric coatings are generally used in combination with drug compounds that are inactivated or destroyed in the stomach, or as a means for delayed release of the drug.

Multiple Compressed Tablets—these are tablets that are made by multiple compression cycles. For example, layered tablets or press-coated tablets. Layered tablets are prepared by compressing additional tablet granulation on a previously compressed granulation. This may be repeated to produce multi-layered tablets. Press-coated tablets are prepared by feeding previously compressed tablets into a tableting machine and compressing a further granulation layer around the preformed tablets. They are generally used to separate incompatible drug substances.

Controlled-Release Tablets—compressed tablets can be formulated so as to release a drug slowly over a prolonged period of time. It is of course also possible to prepare tablets whereby release of the API is immediate or delayed.

Coatings may be used such that the integrity of the dosage form is protected.

As noted above, the composition according to the present invention comprises one or more pharmaceutically acceptable excipients, such as diluent, binder, filler, disintegrant, surfactant, glidant or lubricant. The excipients of the present invention are well known to those of ordinary skill in the art, and details can be found, for example, in Handbook of Pharmaceutical Excipients, 5th Ed., Rowe et al. (eds.), Pharmaceutical Press (2005); Remington: The Science and Practice of Pharmacy, 21st Ed., Lippincott Williams & Wilkins (2005); Current Protocols in Pharmacology, Enna et al. (eds.), John Wiley and Sons, Inc., Hoboken, N.J. (2011).

Fillers and excipients, for example, are commercially available from companies such as Fisher, DFE Pharma, Ashland, Honeywill and Stein, Peter Greven, Aldrich Chemical Co., FMC Corp, Bayer, BASF, Alexi Fres, Witco, Mallinckrodt, Rhodia, ISP, and others.

Active Pharmaceutical Ingredient of the Formulation

Preferably, a provided compound of the invention is as defined in claim 1, but may additionally be a compound where at least one $R^3$ is $NH_2$.

Preferably, $R^1$ is represented by any of the following structures:

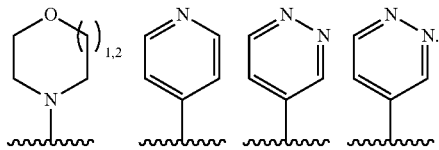

Most preferably, $R^1$ is morpholine.

In a preferred embodiment of the invention, W is oxygen or sulfur, preferably oxygen.

Preferably X is CH.

Preferably $R^3$ is H, $C_1$-$C_{10}$ alkyl, halogen or fluoro $C_1$-$C_{10}$ alkyl. More preferably $R^3$ is H.

Preferably, the 6,5-ring system in Formula I is an indole. In other words, $R^3$ is hydrogen and X is CH.

$R^2$ may be attached to any suitable atom on the aryl group, as depicted in general formula I. However, it is preferred that $R^2$ is attached to the meta-position of the pyridine ring. For example, if the nitrogen atom of the pyridine is labelled as atom number 1, then $R^2$ is attached in the 3-position.

$R^2$ is LY. Preferably, L is $C_1$-$C_{10}$ alkylene, preferably methylene.

Preferably, Y is an optionally substituted bridged or spirocyclic heterocycloalkyl group containing up to 4 heteroatoms selected from N or O, and comprising 5 to 12 atoms in total.

Preferably, Y contains one or two heteroatoms, preferably two heteroatoms. More preferably, at least one of the heteroatoms is nitrogen and Y is bonded to L through the nitrogen atom, as depicted in the preferable Y groups below:

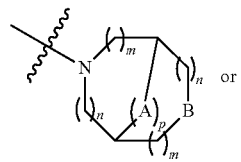

Formula A

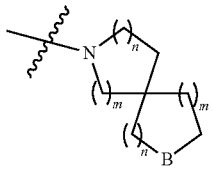

Formula B wherein:
A is selected from the group consisting of O, S, $NR^4$, optionally substituted $C_1$-$C_3$ alkylene, $C_2$-$C_3$ alkenylene and $C_2$-$C_3$ alkynylene;
B is selected from the group consisting of $NR^4$, O and $CH_2$;
wherein $R^4$ is selected from the group consisting of H, optionally substituted $C_1$-$C_{10}$ alkyl, $C_2$-$C_{10}$ alkenyl, $C_2$-$C_{10}$ alkynyl and $C_1$-$C_3$ halofluoroalkyl;
p is selected from 0, 1 or 2;
each m is independently selected from 0, 1 or 2; and
each n is independently selected from 1, 2 or 3.

Preferably, A is O or $C_1$-$C_3$ alkylene, most preferably methylene.

Preferably, B is 0 or $CH_2$, most preferably 0.

When $R^4$ is present, it is preferably H, $C_1$-$C_3$ alkyl or $C_1$-$C_3$ halofluoroalkyl.

More preferably, $R^4$ is H.

Preferably, each m and n is selected so as to form 5-, 6- or 7-membered nitrogen containing heterocycloalkyl groups. Preferably, p is 1. In particular, when A is O, S or $NR^4$, p is 1.

Y is preferably bicyclic, more preferably bridged bicyclic or spirocyclic bicyclic.

Even more preferably, Y is selected from one of the following groups:

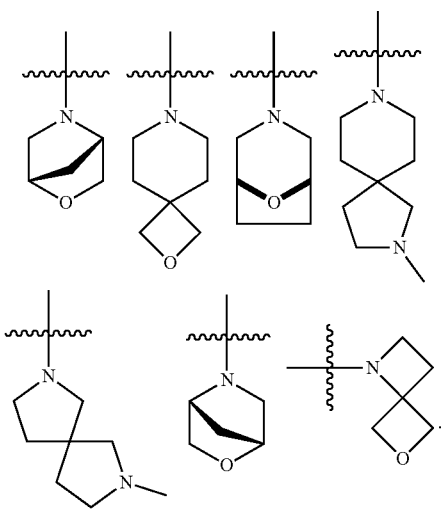

In certain embodiments, provided herein are compounds represented by:

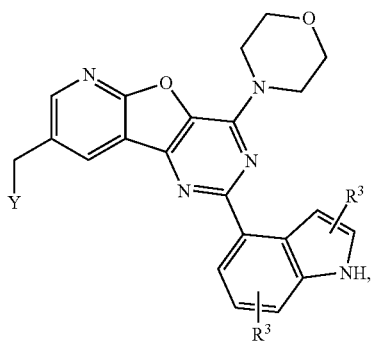

where Y and R³ are defined above.

In another embodiment, provided herein are compositions that include compounds represented by:

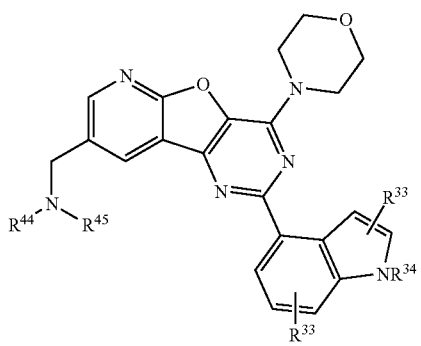

and pharmaceutically acceptable salts thereof,
wherein:
R₃₃ is independently selected for each occurrence from the group consisting of H, halogen, cyano NH—C₁₋₃alkyl, NH₂, C₁₋₆alkyl and —O—C₁₋₆alkyl (wherein C₁₋₆alkyl for each occurrence is optionally substituted by one, two or three substituents selected from halogen and hydroxyl);
R³⁴ is selected from H or C₁₋₃alkyl;
R⁴⁴ and R⁴⁵, when taken together with the nitrogen to which they are attached form a 7-10 membered bicyclic spirocycle or bridged heterocycle each having an additional heteroatom selected from O, S, or NR⁵⁵, wherein R⁵⁵ is H or C₁₋₃alkyl.

For example, R⁴⁴ and R⁴⁵, when taken together with the nitrogen to which they are attached may form a 7-8 membered spirocyclic heterocycle represented by:

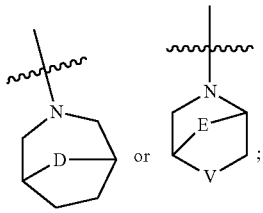

wherein D is O, S or NR⁵⁵, E is O or (CH₂)ᵣ, wherein r is 1 or 2, and V is O or NR⁵⁵, wherein R⁵⁵ is H or C₁₋₃alkyl.

In another exemplary embodiment, R⁴⁴ and R⁴⁵, when taken together with the nitrogen to which they are attached form a 7-10 membered spirocycle having one additional heteroatom selected from O or NR⁵⁵, wherein R⁵⁵ is H or C₁₋₃alkyl. Alternatively, R⁴⁴ and R⁴⁵, taken together with the nitrogen to which they are attached may be a Y substituent as described above.

Examples of structures that may be included in the composition include a compound selected from:

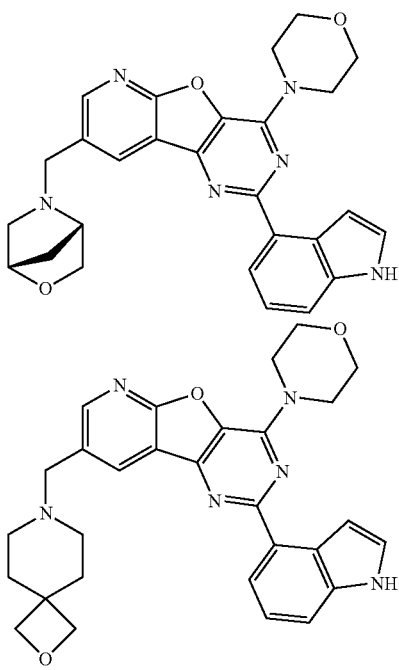

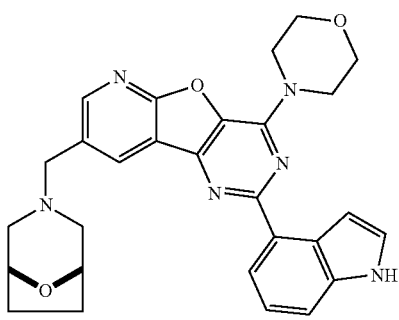

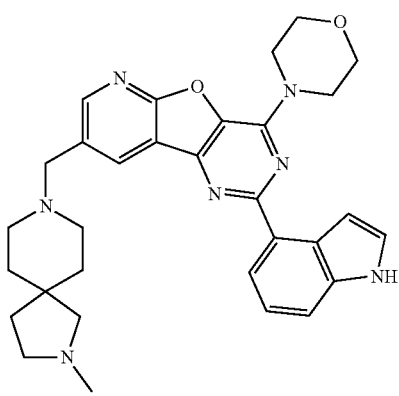

-continued

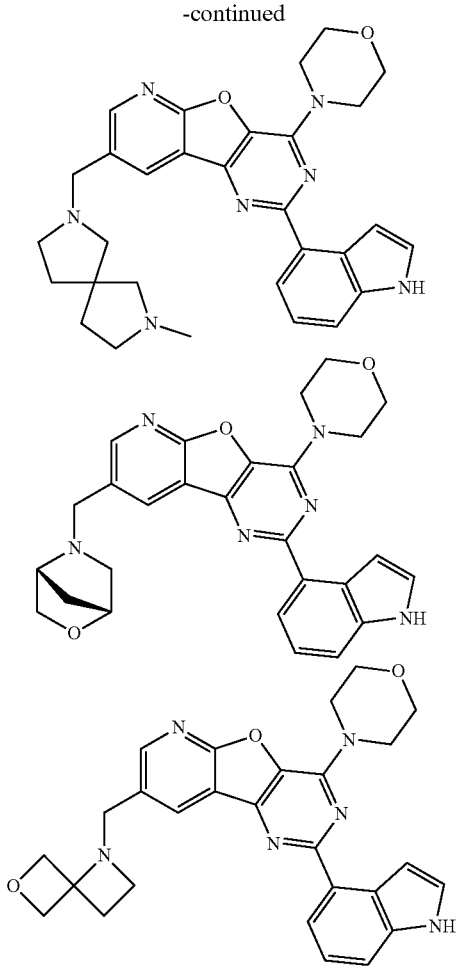

A pharmaceutical composition of the invention typically contains up to 85 wt % of a disclosed compound. More typically, it contains up to 50 wt % of a disclosed compound. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention can be administered orally, for example as tablets, capsules, troches, lozenges, aqueous or oily suspensions, dispersible powders or granules. Preferred pharmaceutical compositions of the invention are compositions suitable for oral administration, for example tablets and capsules.

The compounds of the invention may also be administered by sublingual administration. The present invention therefore also provides a sublingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, *vinca* alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery in a human patient. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Osler-Weber-Rendu syndrome.

Examples of diseases associated with uncontrolled angiogenesis that may be treated according to the present invention include, but are not limited to, retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, Sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulomas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other than the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative and/or PTEN-defective tumours including PTEN-negative haematological, breast, lung, endometrial, skin, brain and prostate cancers (where PTEN refers to "phosphatase and tensin homolog deleted on chromosome 10"). More preferably, the condition to be treated in a patient in need thereof by administering an effective amount of a disclosed compound is a disorder selected from rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. For example, provided herein is a method of treating a patient suffering a disorder selected from the group consisting leukaemias (including e.g., chronic myelogenous leukaemia and acute myeloid leukaemia), lymphoma, a solid tumour cancer such as breast, lung, or prostate cancer, PTEN-negative tumours, including PTEN-negative haematological, breast, lung, endometrial, skin, brain and prostate cancers (where PTEN refers to "phosphatase and tensin homolog deleted on chromosome 10") comprising administering an effective amount of a disclosed compound.

The invention will now be illustrated by the following Examples.

EXAMPLES

Synthesis of Intermediate X (a precursor to the compounds of Formula I)

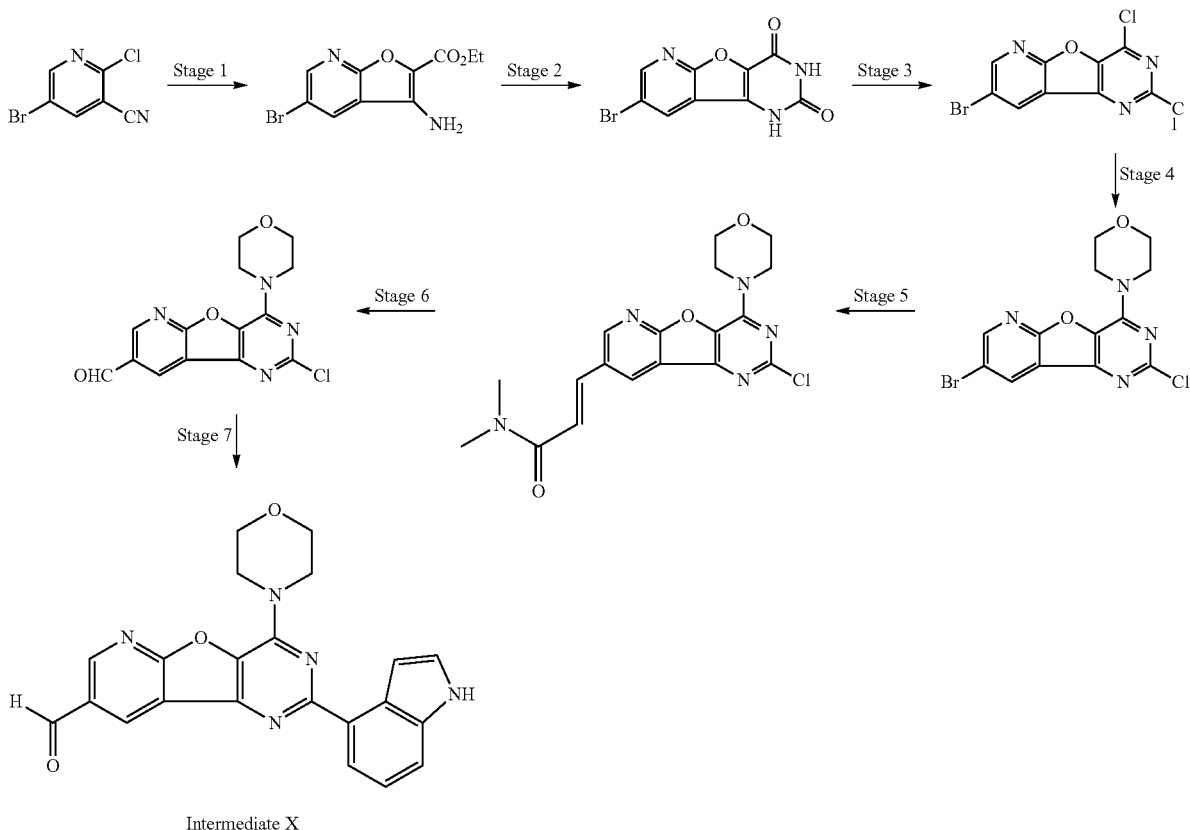

Intermediate X

Reagents and conditions: 1) $K_2CO_3$, ethyl glycolate, DMF, 115° C.; 2) (i) chlorosulfonyl isocyanate, $CH_2Cl_2$, 0-10° C. then rt (ii) water, 75° C. (iii) NaOH max temp 40° C.; 3) $POCl_3$, N,N-dimethylaniline, 107° C.; 4) morpholine, MeOH, rt; 5) N,N,-dimethylacrylamide, $PdCl_2(PPh_3)_2$, NaOAc, DMF, 110° C.; 6) $NaIO_4$, $OsO_4$, THF, water, rt; 7) indole-4-boronic acid pinacol ester, $PdCl_2(PPh_3)_2$, sodium carbonate, dioxane, water, 102° C.

i. Ethyl-3-amino-5-bromofuro[2,3-b]pyridine-2-carboxylate

To a 10 L flask under $N_2(g)$ was added 5-bromo-2-chloropyridine-3-carbonitrile (435 g, 2.0 mol, 1 eq), DMF (2790 mL) and potassium carbonate (553 g, 4.0 mol, 2 eq). This was followed by the addition of ethyl glycolate (208.2 mL, 2.2 mol, 1.1 eq). The reaction mixture was heated to 115° C. overnight. Upon completion, the reaction mixture was cooled to rt and water (13.1 L) was added, this led to the formation of a precipitate. The mixture was stirred for 20 mins, then filtered. The resulting brown solid was dried at 50° C., slurried in $Et_2O$:heptane (9:1, 2.8 L) and filtered to give 405.6 g. Further purification via soxhlet extraction using TBME (4.5 L) yielded the product as a yellow solid (186 g, 34%). This procedure was repeated twice.

$^1$H NMR (400 MHz, $CDCl_3$) $\delta_H$: 8.53 (d, J=2.0 Hz, 1H), 8.07 (d, J=2.0 Hz, 1H), 5.00 (br. s., 2H), 4.44 (q, J=7.0 Hz, 2H), 1.44 (t, J=7.0 Hz, 3H).

MS (ES$^+$) 309 (100%, [M+Na]$^+$), 307 (100%, [M+Na]$^+$).

ii-Bromo-8-oxa-3,5,10-triazatricyclo[7.4.0.0$^{2,7}$]trideca-1(9),2(7),10,12-tetraene-4,6-dione To ethyl-3-amino-5-bromofuro[2,3-b]pyridine-2-carboxylate (239.0 g, 0.84 mol, 1 eq) dissolved in $CH_2Cl_2$ (5.5 L) was added chlorosulfonyl isocyanate (87.6 mL, 1.0 mol, 1.2 eq) dropwise at 0-10° C. The resulting reaction was stirred for 30 min, stripped to dryness and the resulting solid ground to a fine powder. Water (5.5 L) was added to the solid and the suspension was heated at 75° C. for 1 h. After cooling to rt, solid NaOH (335 g, 8.4 mol, 10 eq) was added allowing the reaction to exotherm (maximum temperature 40° C.). The reaction was cooled to 0-10° C. and the pH adjusted to 5-6 using 5M HCl (~1 L). The reaction was stirred for 30 mins, then filtered. The solid was washed with water (2.3 L) and pulled dry. Further drying in a vacuum oven at 40° C. yielded the product as a brown solid (193 g, 76%). This procedure was repeated twice.

$^1$H NMR (400 MHz, DMSO-d$_6$) $\delta_H$: 12.01 (br. s., 1H), 11.58 (br. s, 1H), 8.72 (d, J=2.0 Hz, 1H), 8.59 (d, J=2.0 Hz, 1H). MS (ES$^-$) 282 (100%, [M+H]$^+$).

iii-Bromo-4,6-dichloro-8-oxa-3,5,10-triazatricyclo[7.4.0.0²,⁷]trideca-1(9),2(7),3,5,10,12-hexaene To 12-bromo-8-oxa-3,5,10-triazatricyclo[7.4.0.0²,⁷]trideca-1(9),2(7),10,12-tetraene-4,6-dione (387 g, 1.27 mol, 1 eq) was added POCl₃ (6070 mL) and N,N-dimethylaniline (348 mL, 2.8 mol, 2.2 eq). The mixture was heated at 107° C. for 10 h. Once cooled to rt, solvent was removed in vacuo azeotroping with toluene (3×3.9 L). The resulting residue was partitioned between CH₂Cl₂ (12.76 L) and water (3.9 L) and the phases separated. The organic phase was washed with water (2×3.9 L). The combined aqueous was back-extracted with CH₂Cl₂ (7.7 L) and the combined organics dried over MgSO₄, filtered and stripped to yield the product as brown solid (429 g, ~quant.).
¹H NMR (400 MHz, CDCl₃) δ$_H$: 8.78 (d, J=2.5 Hz, 1H), 8.72 (d, J=2.5 Hz, 1H).

iv. 12-bromo-4-chloro-6-(morpholin-4-yl)-8-oxa-3,5,10-triazatricyclo[7.4.0.0²,⁷]trideca-1(9),2(7),3,5,10,12-hexaene To 12-bromo-4,6-dichloro-8-oxa-3,5,10-triazatricyclo[7.4.0.0²,⁷]trideca-1(9),2(7),3,5,10,12-hexaene (419.3 g, 1.32 mol, 1 eq) in MeOH (8588 mL) was added Morpholine (259 mL, 2.90 mol, 2.2 eq) at rt. After stirring for 2 h, water (0.8 L) was added. It was then cooled to 0-5° C. and stirred for an additional 30 mins. The resulting solid was filtered, washed with water (5.2 L) and pulled dry. Further purification by silica gel column chromatography with CH₂Cl₂/EtOAc (1:0-9:1) yielded the desired product (419 g, 84%).
¹H NMR (400 MHz, CDCl₃) δ$_H$: 8.66 (d, J=2.0 Hz, 1H), 8.62 (d, J=2.0 Hz, 1H), 4.07-4.21 (m, 4H), 3.85-3.91 (m, 4H).
MS (ES⁺) 393 (100%, [M+Na]⁺), 391 (80%, [M+Na]⁺).

v. (2E)-3-[4-Chloro-6-(morpholin-4-yl)-8-oxa-3,5,10-triazatricyclo[7.4.0.0²,⁷]trideca-1(9),2(7),3,5,10,12-hexaen-12-yl]-N,N-dimethylprop-2-enamide To 12-bromo-4-chloro-6-(morpholin-4-yl)-8-oxa-3,5,10-triazatricyclo[7.4.0.0²,⁷]trideca-1(9),2(7),3,5,10,12-hexaene (60 g, 0.15 mol, 1 eq) was added N,N-dimethylacrylamide (16.7 mL, 0.15 mol, 1 eq), PdCl₂(PPh₃)₂ (3.4 g, 4.5 mmol, 0.03 eq) and NaOAc (40 g, 0.45 mol, 3 eq) in DMF (1.2 L). The reaction was heated at 110° C. for 7 h. This process was repeated 3 times and batches combined. Once cooled down to rt, solvent was removed in vacuo and the resulting residue was partitioned between CH₂Cl₂ (6.5 L) and water (5.5 L). The phases were separated and the aqueous phase was extracted with CH₂Cl₂ (2×4 L). The combined organics were washed with brine (2×4 L), dried over MgSO₄, filtered and stripped. The resulting solid was slurried in EtOAc/heptane (1:1, 0.8 L) for 30 mins, filtered, washed and washed with EtOAc/heptane (1:1, 2×450 mL). Further drying in a vacuum oven at 40° C. yielded the desired product as an orange solid (203.0 g, 86%).
¹H NMR (400 MHz, CDCl₃) δ$_H$: 8.70 (s, 2H), 7.82 (d, J=15.6 Hz, 1H), 7.07 (d, J=15.6 Hz, 1H), 4.11-4.19 (m, 4H), 3.85-3.93 (m, 4H), 3.22 (s, 3H), 3.11 (s, 3H).
MS (ES⁺) 388 (100%, [M+H]⁺).

vi. 4-Chloro-6-(morpholin-4-yl)-8-oxa-3,5,10-triazatricyclo[7.4.0.0²,⁷]trideca-1(9),2(7),3,5,10,12-hexaene-12-carbaldehyde (2E)-3-[4-chloro-6-(morpholin-4-yl)-8-oxa-3,5,10-triazatricyclo[7.4.0.0²,⁷]trideca-1(9),2(7),3,5,10,12-hexaen-12-yl]-N,N-dimethylprop-2-enamide (124.0 g, 0.39 mol, 1 eq) was dissolved in THF (12.4 L) at 65° C. Once cooled to 35° C., water (4.1 L), NaIO₄ (205.4 g, 1.17 mol, 3 eq) and OsO₄ (2.5 wt % in tBuOH, 80.3 mL, 2%) were added. The reaction was stirred at rt for 60 h. The reaction was cooled to 0-5° C., stirred for 30 mins then filtered. The solid was washed with water (545 mL) and pulled dry. The crude product was combined with two further batches (2×118.3 g scale) and slurried in water (6.3 L) for 30 mins at rt. The solids were filtered, washed with water (1.6 L) and pulled dry. Further drying in a vacuum oven yielded the desired product as a pink solid (260 g, 88%)
¹H NMR (400 MHz, CDCl₃:MeOD, 9:1) δ$_H$: 10.13 (s, 1H), 9.04 (d, J=2.0 Hz, 1H), 8.91 (d, J=2.0 Hz, 1H), 3.99-4.13 (m, 4H), 3.73-3.84 (m, 4H).
MS (ES⁺) 351 (100%, [M+MeOH+H]⁺).

vii. 4-(1H-Indol-4-yl)-6-(morpholin-4-yl)-8-oxa-3,5,10-triazatricyclo[7.4.0.0²,⁷]trideca-1(9),2,4,6,10,12-hexaene-12-carbaldehyde To 4-chloro-6-(morpholin-4-yl)-8-oxa-3,5,10-triazatricyclo[7.4.0.0²,⁷]trideca-1(9),2(7),3,5,10,12-hexaene-12-carbaldehyde (164.4 g, 0.52 mol, 1 eq) was added indole-4-boronic acid pinacol ester (376.0 g, 1.55 mol, 3 eq), PdCl₂(PPh₃)₂ (72.0 g, 0.10 mol, 2 eq) and sodium carbonate (110.2 g, 1.04 mol, 2 eq) in dioxane (16.4 L)/water (5.8 L). Reaction mixture was refluxed for 1 h. It was then cooled to 60-70° C. Water (9.8 L), brine (4.9 L) and EtOAc (9.5 L) were added. The phases were separated and the aqueous phase extracted with EtOAc (3×9.5 L) at 60-65° C. The combined organics were dried over MgSO₄, filtered and stripped. The resulting solid was slurried in CH₂Cl₂ (4.75 L) for 30 mins, filtered, washed with CH₂Cl₂ (3×238 mL) and pulled dry. Further drying in a vacuum oven at 40° C. yielded Intermediate X as a yellow solid (135.7 g, 66%).
¹H NMR (300 MHz, CDCl₃) δ$_H$: 11.27 (br. s, 1H), 10.26 (s, 1H), 9.16 (d, J=2.3 Hz, 1H), 9.11 (d, J=2.3 Hz, 1H), 8.18 (d, J=7.5 Hz, 1H), 7.58-7.67 (m, 2H), 7.49 (t, J=2.8 Hz, 1H), 7.23 (t, J=7.7 Hz, 1H), 4.08-4.16 (m, 4H), 3.83-3.90 (m, 4H).
MS (ES⁺) 432.0 (100%, [M+MeOH+H]⁺).

Synthesis of Examples of the Present Invention

Example A 4-(1H-Indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0²,⁷]trideca-1(13),2(7),3,5,9,11-hexaene

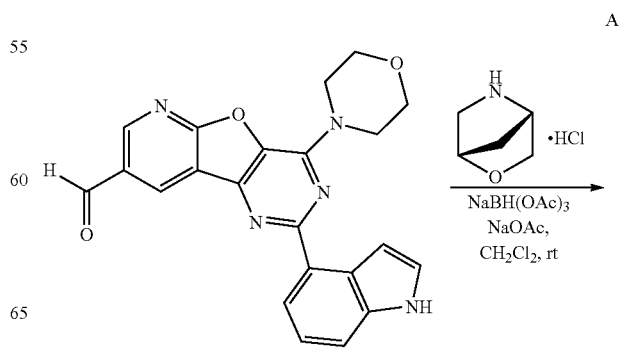

-continued

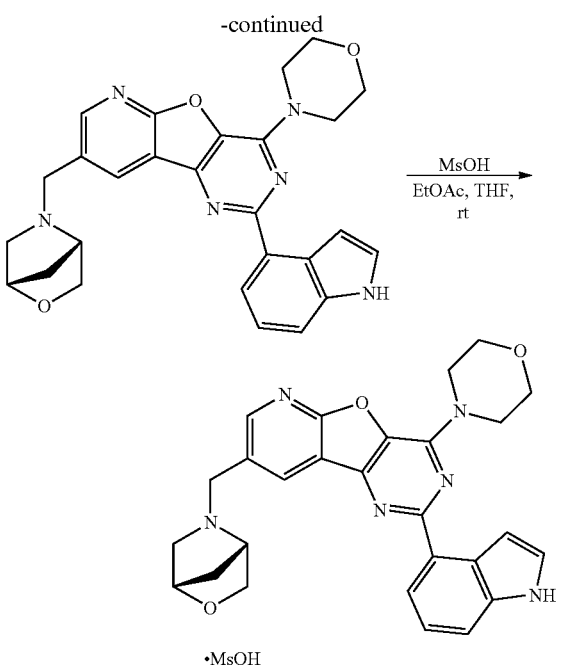

To a suspension of intermediate X (7.00 g, 17.53 mmol, 1 eq), (1S,4S)-2-oxa-5-azabicyclo[2.2.1]heptane hydrochloride (7.13 g, 52.58 mmol, 3 eq) and NaOAc (4.31 g, 52.58 mmol, 3 eq) in anhydrous CH$_2$Cl$_2$ (150 mL) was added NaBH(OAc)$_3$ (7.43 g, 35.06 mmol, 2 eq). The reaction mixture was stirred at rt overnight. Then, it was partitioned with 1N NaOH (100 mL) and extracted with CH$_2$Cl$_2$ (3×200 mL). The combined organic extracts were washed with brine (50 mL) then dried over MgSO$_4$ and the solvent was removed in vacuo. Purification by silica gel column chromatography with EtOAc/MeOH (1:0-7:1) yielded the product A as a white solid (6.02 g, 71%).

$^1$H NMR (300 MHz, CDCl$_3$) δ$_H$: 8.65 (d, J=2.1 Hz, 1H), 8.58 (d, J=2.1 Hz, 1H), 8.37 (br. s., 1H), 8.24 (dd, J=7.5, 0.9 Hz, 1H), 7.62 (td, J=2.6, 0.8 Hz, 1H), 7.53 (d, J=8.1 Hz, 1H), 7.37-7.41 (m, 1H), 7.31-7.37 (m, 1H), 4.47 (s, 1H), 4.22-4.30 (m, 4H), 4.18 (d, J=8.1 Hz, 1H), 3.98 (d, J=2.3 Hz, 2H), 3.91-3.97 (m, 4H), 3.70 (dd, J=7.9, 1.7 Hz, 1H), 3.53 (s, 1H), 2.94 (dd, J=10.0, 1.5 Hz, 1H), 2.64 (d, J=10.2 Hz, 1H), 1.97 (dd, J=9.8, 1.9 Hz, 1H), 1.80 (dt, J=9.8, 1.1 Hz, 1H).
MS (ES$^+$) 483.1 (100%, [M+H]$^+$).

4-(1H-Indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene; methanesulfonic acid A (5.98 g, 12.38 mmol, 1 eq) was dissolved in hot EtOAc (1 L) and THF (200 mL). Once cooled down to rt, a solution of MsOH (884 µL, 13.6 mmol, 1.1 eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of A was obtained as a yellow solid (6.50 g, 91%).

$^1$H NMR (300 MHz, DMSO-d$_6$) δ$_H$: 11.33 (br. s., 1H), 9.69-10.24 (m, 1H), 9.05 (d, J=2.1 Hz, 1H), 8.79-8.93 (m, 1H), 8.19 (d, J=7.5 Hz, 1H), 7.54-7.62 (m, 2H), 7.50 (t, J=2.7 Hz, 1H), 7.24 (t, J=7.7 Hz, 1H), 4.64-4.89 (m, 2H), 4.47-4.61 (m, 2H), 4.14 (m, 4H), 3.94-4.00 (m, 2H), 3.83-3.91 (m, 4H), 3.72-3.83 (m, 1H), 3.29-3.46 (m, 2H), 2.33 (s, 4H), 2.02-2.15 (m, 1H).
MS (ES$^+$) 483.1 (100%, [M−MsOH+H]$^+$).

Example B 4-(1H-Indol-4-yl)-6-(morpholin-4-yl)-12-{2-oxa-7-azaspiro[3.5]nonan-7-ylmethyl}-8-oxa-3,5,10-triazatricyclo[7.4.0.0$^{2,7}$]trideca-1(13),2(7),3,5,9,11-hexaene

B

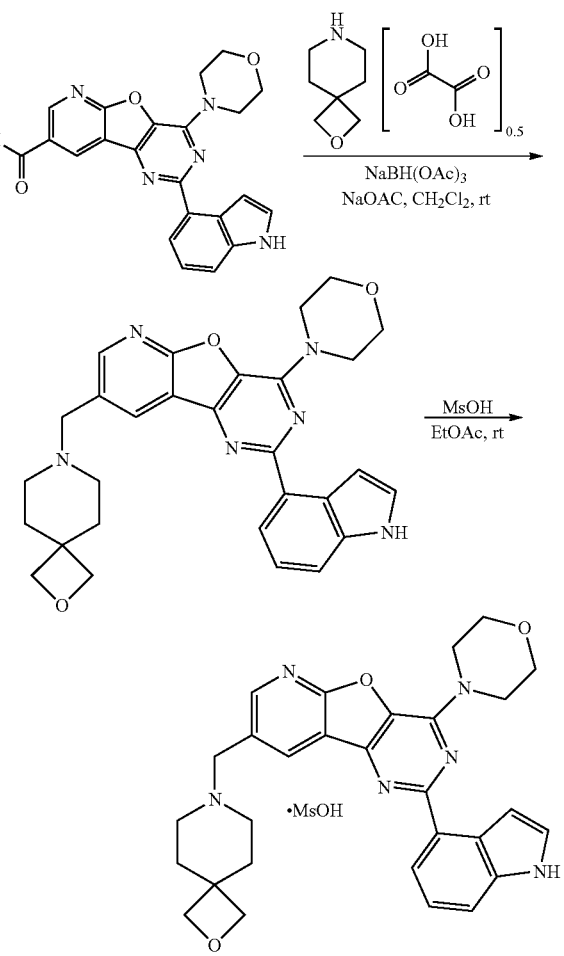

To a suspension of intermediate X (3.108 g, 7.78 mmol 1 eq), 2-oxa-7-azaspiro[3.5]nonane hemioxalate (4.02 g, 23.3 mmol, 3 eq) and NaOAc (1.91 g, 23.3 mmol, 3 eq) in anhydrous CH$_2$Cl$_2$ (280 mL) was added NaBH(OAc)$_3$ (3.30 g, 15.6 mmol, 2 eq). The reaction mixture was stirred at rt overnight. Then, it was partitioned with 1N NaOH (150 mL) and extracted with CH$_2$Cl$_2$ (2×100 mL). The combined organic extracts were washed with 50% brine (100 mL) then dried over MgSO$_4$ and the solvent was removed in vacuo. Purification by silica gel column chromatography with EtOAc/MeOH (1:0-8:1) yielded the product B as an off-white solid (3.154 g, 79%).

¹H NMR (300 MHz, CDCl₃) δ$_H$: 8.59 (d, J=2.1 Hz, 1H), 8.53 (d, J=1.9 Hz, 1H), 8.41 (br. s., 1H), 8.24 (dd, J=7.4, 0.8 Hz, 1H), 7.61 (t, J=2.3 Hz, 1H), 7.53 (d, J=8.1 Hz, 1H), 7.37-7.41 (m, 1H), 7.34 (t, J=7.9 Hz, 1H), 4.43 (s, 4H), 4.22-4.30 (m, 4H), 3.86-4.00 (m, 4H), 3.68 (s, 2H), 2.23-2.59 (m, 4H), 1.83-2.00 (m, 4H).
MS (ES⁺) 511.1 (100%, [M+H]⁺).

4-(1H-Indol-4-yl)-6-(morpholin-4-yl)-12-{2-oxa-7-azaspiro[3.5]nonan-7-ylmethyl}-8-oxa-3,5,10-triazatricyclo[7.4.0.0²,⁷]trideca-1(13),2(7),3,5,9,11-hexaene; methanesulfonic acid To a solution of B (2.987 g, 5.854 mmol, 1 eq) in EtOAc (1.2 L, heat to 70° C. for 5 min to dissolve) at rt was added a solution of MsOH (590 μL, 6.14 mmol, 1.05 eq) in EtOAc (16 mL). A yellow precipitate formed instantly. The suspension was shaken vigorously for 20 s then left to stand at rt overnight. The excess supernatant was decanted off (600 mL), then EtOAc was added (500 mL). The suspension was shaken again and left to stand for 1 h before another 500 mL of excess supernatant was decanted off. The solvent was removed in vacuo to give the salt form of F as a yellow solid (3.230 g, 91%).
¹H NMR (300 MHz, DMSO-d₆) δ$_H$: 11.33 (br. s., 1H), 9.45 (br. s., 1H), 8.90 (d, J=1.9 Hz, 1H), 8.72 (d, J=1.9 Hz, 1H), 8.19 (d, J=7.3 Hz, 1H), 7.41-7.69 (m, 3H), 7.23 (t, J=7.8 Hz, 1H), 4.58 (d, J=3.8 Hz, 2H), 4.39 (s, 2H), 4.29 (s, 2H), 4.03-4.22 (m, 4H), 3.81-3.97 (m, 4H), 3.40 (d, J=12.1 Hz, 2H), 2.88-3.13 (m, 2H), 2.33 (s, 3H), 2.26 (d, J=13.9 Hz, 2H), 1.69-1.91 (m, 2H).
MS (ES⁺) 511.1 (100%, [M−MsOH+H]⁺).

Example C 4-(1H-Indol-4-yl)-6-(morpholin-4-yl)-12-{8-oxa-3-azabicyclo[3.2.1]octan-3-ylmethyl}-8-oxa-3,5,10-triazatricyclo[7.4.0.0²,⁷]trideca-1(13),2(7),3,5,9,11-hexaene To a suspension of intermediate X (100 mg, 0.25 mmol, 1 eq), 8-oxa-3-azabicyclo[3.2.1]octane hydrochloride (112 mg, 0.75 mmol, 3 eq) and NaOAc (62 mg, 0.75 mmol, 3 eq) in anhydrous CH₂Cl₂ (10 mL) was added NaBH(OAc)₃ (106 mg, 0.50 mmol, 2 eq). The reaction mixture was stirred at rt overnight. Then, it was partitioned with 1N NaOH (10 mL), extracted with CH₂Cl₂ (3×10 mL). The combined organic extracts were washed with brine (10 mL) then dried over MgSO₄ and the solvent was removed in vacuo. Purification by silica gel column chromatography with EtOAc/MeOH (1:0-49:1) yielded the product C as an off white solid (116 mg, 93%).
¹H NMR (300 MHz, CDCl₃) δ$_H$: 8.56 (d, J=3.6 Hz, 2H), 8.35 (br. s., 1H), 8.24 (d, J=7.5 Hz, 1H), 7.58-7.66 (m, 1H), 7.51-7.57 (m, 1H), 7.31-7.44 (m, 2H), 4.30-4.38 (m, 2H), 4.23-4.30 (m, 4H), 3.89-4.01 (m, 4H), 3.68 (s, 2H), 2.61 (d, J=10.7 Hz, 2H), 2.40-2.52 (m, 2H), 1.96-2.09 (m, 2H), 1.83-1.95 (m, 2H).
MS (ES⁺) 497.1 (100%, [M+H]⁺).

Example D 4-(1H-Indol-4-yl)-12-({2-methyl-2,8-diazaspiro[4.5]decan-8-yl}methyl)-6-(morpholin-4-yl)-8-oxa-3,5,10-triazatricyclo[7.4.0.0²,⁷]trideca-1(13),2(7),3,5,9,11-hexaene

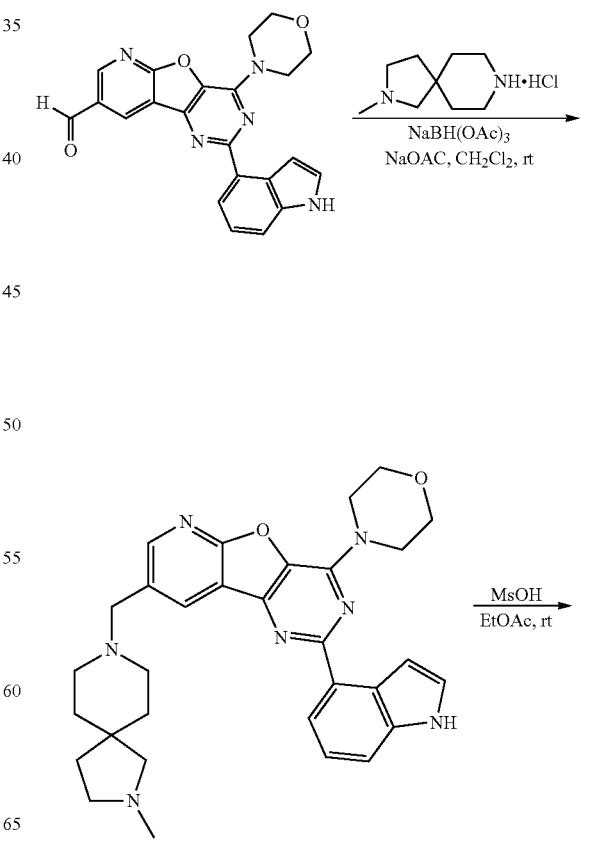

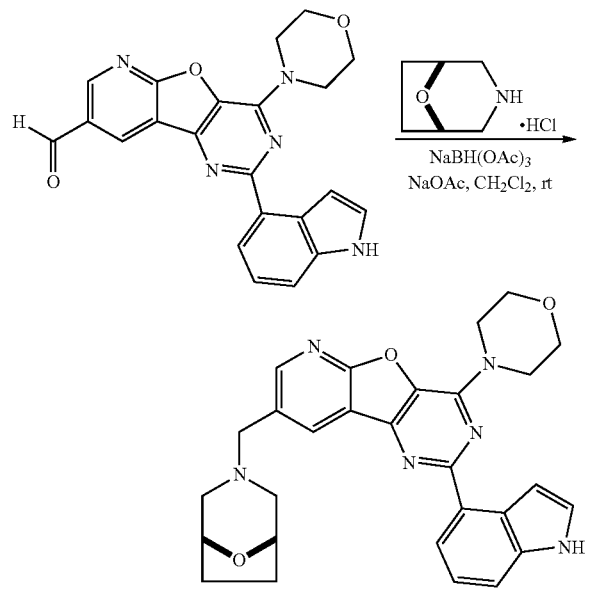

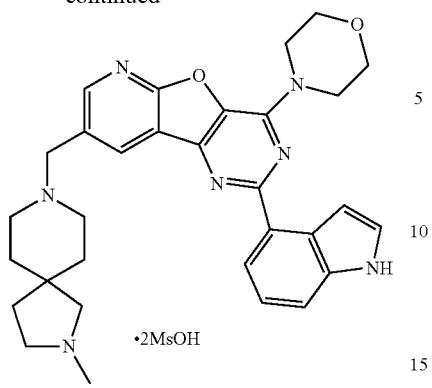

To a suspension of intermediate X (1.02 g, 2.55 mmol, 1 eq), 2-methyl-2,8-diazaspiro[4.5]decane hydrochloride (1.46 g, 7.66 mmol, 3 eq) and NaOAc (628 mg, 7.66 mmol, 3 eq) in anhydrous $CH_2Cl_2$ (100 mL) was added $NaBH(OAc)_3$ (1.08 g, 5.1 mmol, 2 eq). The reaction mixture was stirred at rt overnight. Then, it was partitioned with 1N NaOH (30 mL) and extracted with $CH_2Cl_2$ (3×50 mL). The combined organic extracts were washed with brine (10 mL) then dried over $MgSO_4$ and the solvent was removed in vacuo. Purification by silica gel column chromatography with $CH_2Cl_2$/MeOH (0:1-4:1) yielded the product D as a white solid (890 mg, 65%).

$^1$H NMR (300 MHz, $CDCl_3$) $\delta_H$: 8.60 (d, J=2.1 Hz, 1H), 8.54 (d, J=2.1 Hz, 1H), 8.39 (br. s., 1H), 8.24 (dd, J=7.4, 0.8 Hz, 1H), 7.62 (t, J=2.3 Hz, 1H), 7.53 (d, J=8.1 Hz, 1H), 7.38 (t, J=2.8 Hz, 1H), 7.30-7.37 (m, 1H), 4.21-4.31 (m, 4H), 3.89-3.99 (m, 4H), 3.69 (s, 2H), 2.59 (t, J=6.8 Hz, 2H), 2.38-2.50 (m, 5H), 2.35 (s, 3H), 1.54-1.73 (m, 7H).

MS ($ES^+$) 538.2 (100%, $[M+H]^+$).

4-(1H-Indol-4-yl)-12-({2-methyl-2,8-diazaspiro[4.5]decan-8-yl}methyl)-6-(morpholin-4-yl)-8-oxa-3,5,10-triazatricyclo[7.4.0.0$^{2,7}$]trideca-1 (13),2(7),3,5,9,11-hexaene; bis(methanesulfonic acid)

Compound D (821 mg, 1.52 mmol, 1 eq) was dissolved in hot EtOAc (400 mL). Once cooled down to rt, a solution of MsOH (218 μL, 3.36 mmol, 2.2 eq) in EtOAc (5 mL) was added slowly. An instant yellow precipitate formed. The suspension was shaken vigorously for 10 s then left to stand at rt overnight. As solid settled, excess supernatant was decanted off (200 mL), then EtOAc was added (200 mL). The suspension was shaken again and left to stand for 1 h. This operation was repeated twice, then the solvent was removed in vacuo. The salt form of D was obtained as a yellow solid (1.037 g, 93%).

$^1$H NMR (300 MHz, DMSO-$d_6$) $\delta_H$: 11.32 (br. s., 1H), 9.46-10.03 (m, 2H), 8.93 (d, J=2.1 Hz, 1H), 8.76 (d, J=1.7 Hz, 1H), 8.19 (dd, J=7.4, 0.7 Hz, 1H), 7.53-7.60 (m, 2H), 7.50 (t, J=2.6 Hz, 1H), 7.24 (t, J=7.8 Hz, 1H), 4.63 (br. s., 2H), 4.10-4.20 (m, 4H), 3.82-3.91 (m, 5H), 3.54-3.77 (m, 2H), 3.36-3.51 (m, 2H), 3.05-3.25 (m, 3H), 2.89-3.03 (m, 1H), 2.80-2.89 (m, 3H), 2.36 (s, 6H), 2.02-2.17 (m, 1H), 1.65-1.95 (m, 4H).

MS ($ES^+$) 538.2 (100%, [M−2MsOH+H]$^+$).

Example E 4-(1H-Indol-4-yl)-12-({7-methyl-2,7-diazaspiro[4.4]nonan-2-yl}methyl)-6-(morpholin-4-yl)-8-oxa-3,5,10-triazatricyclo[7.4.0.0$^{2,7}$]trideca-1(13),2(7),3,5,9,11-hexaene

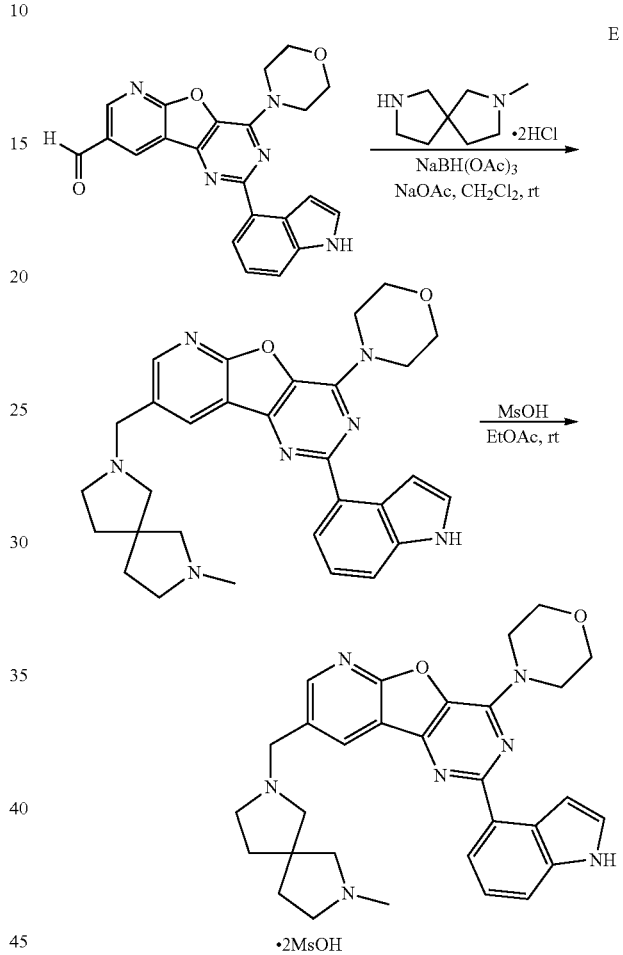

To a suspension of intermediate X (250 mg, 0.63 mmol, 1 eq), 2-methyl-2,7-diazaspiro[4.4]nonane dihydrochloride (400 mg, 1.87 mmol, 3 eq) and NaOAc (305 mg, 3.70 mmol, 6 eq) in anhydrous $CH_2Cl_2$ (20 mL) was added $NaBH(OAc)_3$ (265 mg, 1.25 mmol, 2 eq). The reaction mixture was stirred at rt overnight. Then, it was partitioned with 1N NaOH (10 mL), extracted with $CH_2Cl_2$ (3×10 mL) and EtOAc (10 mL). The combined organic extracts were washed with brine (10 mL) then dried over $MgSO_4$ and the solvent was removed in vacuo. Purification by silica gel column chromatography with $CH_2Cl_2$/MeOH (0:1-4:1) yielded the product E as a white solid (169 mg, 52%).

$^1$H NMR (300 MHz, $CDCl_3$) $\delta_H$: 8.58 (d, J=2.1 Hz, 1H), 8.53 (d, J=2.1 Hz, 1H), 8.48 (br. s., 1H), 8.23 (dd, J=7.4, 0.8 Hz, 1H), 7.63 (t, J=2.2 Hz, 1H), 7.53 (d, J=7.9 Hz, 1H), 7.39 (t, J=2.7 Hz, 1H), 7.29-7.36 (m, 1H), 4.21-4.30 (m, 4H), 3.89-3.99 (m, 4H), 3.72-3.85 (m, 2H), 2.49-2.83 (m, 8H), 2.45 (s, 3H), 1.81-2.06 (m, 4H).

MS ($ES^+$) 524.1 (100%, $[M+H]^+$).

4-(1H-Indol-4-yl)-12-({7-methyl-2,7-diazaspiro[4.4]
nonan-2-yl}methyl)-6-(morpholin-4-yl)-8-oxa-3,5,
10-triazatricyclo[7.4.0.0²,⁷]trideca-1(13),2(7), 3,5,9,
11-hexaene; bis(methanesulfonic acid)

Compound E (129 mg, 0.25 mmol, 1 eq) was dissolved in hot EtOAc (50 mL). Once cooled down to rt, a solution of MsOH (354, 0.54 mmol, 2.2 eq) in EtOAc (2 mL) was added slowly. An instant yellow precipitate formed. The suspension was shaken vigorously for 10 s then left to stand at rt overnight. As solid settled, excess supernatant was decanted off (20 mL), then EtOAc was added (20 mL). The suspension was shaken again and left to stand for 1 h. This operation was repeated twice, then the solvent was removed in vacuo. The salt form of E was obtained as a yellow solid (173 mg, 98%).

$^1$H NMR (300 MHz, DMSO-d$_6$) δ$_H$: 11.33 (br. s., 1H), 10.39 (br. s., 1H), 9.72-10.12 (m, 1H), 8.73-9.09 (m, 2H), 8.19 (d, J=7.5 Hz, 1H), 7.41-7.63 (m, 3H), 7.24 (t, J=7.8 Hz, 1H), 4.53-4.87 (m, 2H), 4.10-4.22 (m, 4H), 3.79-3.93 (m, 4H), 3.32-3.77 (m, 6H), 2.99-3.29 (m, 2H), 2.78-2.89 (m, 3H), 2.36 (s, 6H), 1.87-2.22 (m, 3H).
MS (ES$^+$) 524.5 (100%, [M−2MsOH+H]$^+$).

Example F 4-(1H-Indol-4-yl)-6-(morpholin-4-yl)-12-[(1R,4R)-
2-oxa-5-azabicyclo[2.2.1]heptan-5-ylmethyl]-8-oxa-
3,5,10-triazatricyclo[7.4.0.0²,⁷]trideca-1(13),2(7),3,
5,9,11-hexaene

F

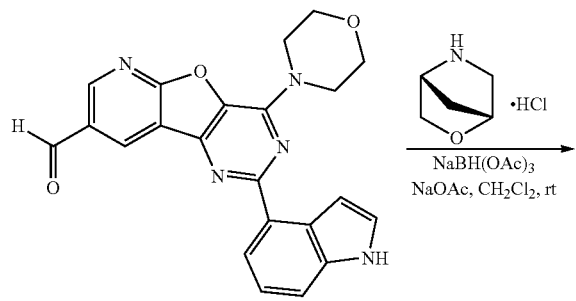

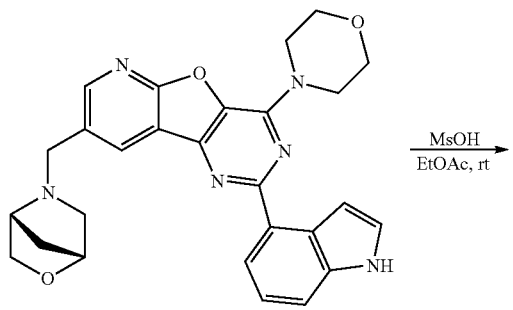

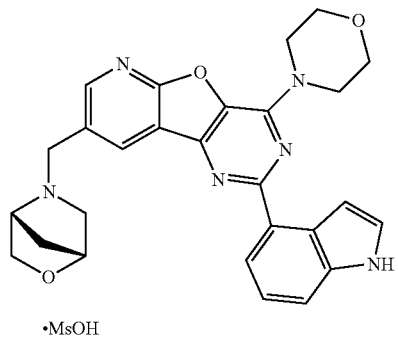

·MsOH

To a suspension of intermediate X (200 mg, 0.50 mmol, 1 eq), (1R,4R)-2-oxa-5-azabicyclo[2.2.1]heptane hydrochloride (204 mg, 1.50 mmol, 3 eq) and NaOAc (123 mg, 1.5 mmol, 3 eq) in anhydrous CH$_2$Cl$_2$ (10 mL) was added NaBH(OAc)$_3$ (160 mg, 0.76 mmol, 2 eq). The reaction mixture was stirred at rt overnight. Then, it was partitioned with 1N NaOH (20 mL) and extracted with CH$_2$Cl$_2$ (3×20 mL). The combined organic extracts were passed through a phase separator and the solvent was removed in vacuo. Purification by silica gel column chromatography with EtOAc/MeOH (1:0-9:1) yielded the product F as a white solid (141.1 mg, 59%).

$^1$H NMR (400 MHz, CDCl$_3$) δ$_H$: 8.64 (d, J=2.1 Hz, 1H), 8.57 (d, J=2.1 Hz, 1H), 8.35 (br. s., 1H), 8.23 (dd, J=7.5, 0.9 Hz, 1H), 7.62 (m, 1H), 7.53 (d, J=8.1 Hz, 1H), 7.36-7.39 (m, 1H), 7.31-7.36 (m, 1H), 4.46 (s, 1H), 4.25 (m, 4H), 4.18 (d, J=8.1 Hz, 1H), 3.97 (d, J=2.3 Hz, 2H), 3.93-3.97 (m, 4H), 3.68 (dd, J=7.9, 1.7 Hz, 1H), 3.53 (s, 1H), 2.93 (dd, J=10.0, 1.5 Hz, 1H), 2.62 (d, J=10.2 Hz, 1H), 1.95 (dd, J=9.8, 1.9 Hz, 1H), 1.79 (dt, J=9.8, 1.1 Hz, 1H).
MS (ES$^+$) 483.1 (100%, [M+H]$^+$).

4-(1H-Indol-4-yl)-6-(morpholin-4-yl)-12-[(1R,4R)-
2-oxa-5-azabicyclo[2.2.1]heptan-5-ylmethyl]-8-oxa-
3,5,10-triazatricyclo[7.4.0.0²,⁷]trideca-1(13),2(7),3,
5,9,11-hexaene; methanesulfonic acid Compound F (141 mg, 0.29 mmol, 1 eq) was dissolved in hot EtOAc (100 mL) then treated with 0.87 ml of a 0.308M MsOH solution in EtOAc under vigorously swirling. The mixture was set aside overnight. The excess supernatant was decanted (using a small Pasteur pipette) and more EtOAc (50 mL) was added. The suspension was once again shaken vigorously then left to stand at rt overnight. The excess supernatant was once more decanted and the solvent was removed in vacuo. The resulting solid was dried in a vacuum oven at 40° C. The salt form of F was obtained as a yellow solid (160 mg, 95%).

$^1$H NMR (400 MHz, DMSO-d$_6$) δ$_H$: 11.33 (br. s., 1H), 9.65-10.16 (m, 1H), 9.05 (d, J=2.0 Hz, 1H), 8.83-8.90 (m, 1H), 8.20 (d, J=7.3 Hz, 1H), 7.58-7.61 (m, 1H), 7.56 (d, J=7.8 Hz, 1H), 7.51 (t, J=2.8 Hz, 1H), 7.23 (t, J=7.7 Hz, 1H), 4.82 (dd, J=13.1, 4.5 Hz, 1H), 4.65-4.76 (m, 1H), 4.50-4.59 (m, 2H), 4.11-4.19 (m, 4H), 3.99 (d, J=9.6 Hz, 1H), 3.88 (t, J=4.5 Hz, 4H), 3.78 (dd, J=9.5, 1.4 Hz, 1H), 3.31-3.38 (m, 2H), 2.52-2.57 (m, 1H), 2.30 (s, 3H), 2.02-2.18 (m, 1H).
MS (ES$^+$) 483.2 (100%, [M−MsOH+H]$^+$).

Example G 4-(1H-indol-4-yl)-6-(morpholin-4-yl)-12-{6-oxa-1-azaspiro[3.3]heptan-1-ylmethyl}-8-oxa-3,5,10-triazatricyclo[7.4.0.0²,⁷]trideca-1(13),2(7),3,5,9,11-hexaene

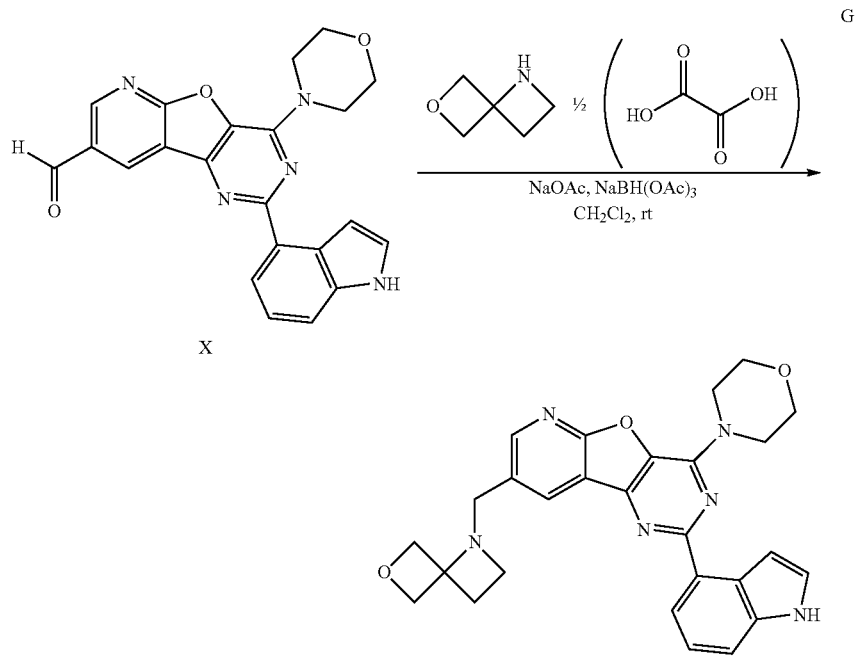

Intermediate X (125 mg, 0.31 mmol), 6-oxa-1-azaspiro[3.3]heptane hemioxalate (134 mg, 0.93 mmol, 3 eq) and NaOAc (76 mg, 0.93 mmol, 3 eq) were suspended in CH$_2$Cl$_2$ (16 mL) at rt. The mixture was stirred for 15 mins then NaBH(OAc)$_3$ (131 mg, 0.62 mmol, 2 eq) was added. The resulting suspension was stirred at rt overnight. The reaction mixture was then partitioned with 0.5 N NaOH (8 mL) and extracted with CH$_2$Cl$_2$ (2×10 mL). The combined organics were washed with 50% brine (5 mL) then dried over MgSO$_4$ and the solvent was removed in vacuo. The residue was dissolved in DMSO (2 mL) and purified by basic preparative LCMS to yield G as a white solid (48 mg, 32%).

$^1$H NMR (DMSO-d$_6$) δ$_H$: 11.30 (br s, 1H), 8.62 (s, 2H), 8.18 (d, J=7.6 Hz, 1H), 7.51-7.58 (m, 2H), 7.46-7.51 (m, 1H), 7.22 (t, J=7.7 Hz, 1H), 4.89 (d, J=7.6 Hz, 2H), 4.55 (d, J=7.3 Hz, 2H), 4.08-4.17 (m, 4H), 4.03 (s, 2H), 3.81-3.91 (m, 4H), 3.03 (t, J=6.7 Hz, 2H), 2.32 (t, J=6.7 Hz, 2H).

MS (ES$^+$) 483.3 (100%, [M+H]$^+$).

Biological Data

Fold form selectivity inhibition data against class I PI3K isoforms, as determined using a HTRF biochemical assay conducted at Reaction Biology Corp., is listed below.

| | Fold IC$_{50}$ | | | |
|---|---|---|---|---|
| Example | p110β/p110α | p110β/p110γ | p110δ/p110α | p110δ/p110γ |
| A | * | ** | * | ** |
| B | ** | ** | ** | ** |
| C | * | ** | ** | ** |
| D | ** | ** | ** | ** |

| | Fold IC$_{50}$ | | | |
|---|---|---|---|---|
| Example | p110β/p110α | p110β/p110γ | p110δ/p110α | p110δ/p110γ |
| E | ** | ** | ** | ** |
| F | * | * | ** | ** |
| G | * | ** | ** | ** |

Key:
* = ≥10× ≥ 50×;
** = >50×

Rodent Pharmacokinetic Comparative Data

Disclosed compounds have increased bioavailability and reduced clearance (data below for mice).

Example A

The following protocol was used to determine oral bioavailability and clearance, and the results are shown below:
- Species=male mouse;
- Strain=CD1;
- n=3 male mice per time point per route;
- Terminal blood sampling at 8 time points (5 min, 10 min, 0.5 hr, 1 hr, 3 hr, 6 hr, 8 hr and, 24 hr);
- Collection of plasma, bio-analysis and report of pharmacokinetic parameters.
- Formulation: 10% DMSO, 90% Saline
- Dosing: 10 mg/kg P.O. and 5 mg/kg I.V.

| Plasma PK Summary: | |
|---|---|
| | Value—Mesylate Salt |
| Parameters—IV, 5 mg/kg | |
| $t_{1/2}$ (hr) | 1.3 |
| $T_{max}$ (hr) | 0.08 |
| $C_{max}$ (ng/mL) | 2640 |
| $AUC_{last}$ (hr*ng · mL) | 3905 |
| $AUC_{all}$ (hr*ng/mL) | 3905 |
| $AUC_{inf}$ (hr*ng/mL) | 3946 |
| Clearance (mL/hr/Kg) | 1267 |
| Vd (mL/Kg) | 2441 |
| Parameters—PO, 10 mg/kg | |
| $t_{1/2}$ (hr) | 1.3 |
| $T_{max}$ (hr) | 1.00 |
| $C_{max}$ (ng/mL) | 1973 |
| $AUC_{last}$ (hr*ng/mL) | 5625 |
| $AUC_{all}$ (hr*ng/mL) | 5625 |
| $AUC_{inf}$ (hr* ng/mL) | 5822 |
| F | 73.77% |

Example A

Oral bioavailability (F)=74%
Clearance=21 mL/min/kg

Example B

The following protocol was used to determine oral bioavailability and clearance, and the results are shown below:
  Species=male mouse;
  Strain=Balb/c;
  18 male mice were divided into two groups Group 1 (3 mg/kg; I.V.), Group 2 (10 mg/kg; P.O.) with each group comprising nine mice;
  Blood samples (approximately 60 μL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);
  The blood samples were collected from a set of three mice at each time point in labeled micro centrifuge tube containing K2EDTA as anticoagulant;
  Plasma samples were separated by centrifugation of whole blood and stored below −70° C. until bioanalysis;
  All samples were processed for analysis by protein precipitation using acetonitrile (ACN) and analyzed with fit for purpose LC/MS/MS method (LLOQ: 2.02 ng/mL);

Pharmacokinetic parameters were calculated using the non-compartmental analysis tool of Phoenix WinNonlin (Version 6.3).
Formulation:
Animals in Group 1 were administered intravenously with Example B solution formulation in 20% propylene glycol, 50% of PEG 400 and 30% of 20% βCD in water via tail vein at a dose of 3 mg/kg.
Animals in Group 2 were administered with oral solution formulation of Example B in 20% propylene glycol, 50% of PEG 400 and 30% of 20% HPβCD in water at a dose of 10 mg/kg;
Dosing: 10 mg/kg P.O. and 3 mg/kg I.V.

| Plasma PK Summary: | |
|---|---|
| | Value—Mesylate Salt |
| Parameters—IV, 3 mg/kg | |
| $t_{1/2}$ (hr) | 1.23 |
| $C_{max}$ (ng/mL) | 621.42 |
| $AUC_{last}$ (hr*ng · mL) | 1512.20 |
| $AUC_{inf}$ (hr*ng/mL) | 1512.20 |
| Clearance (mL/hr/Kg) | 1983.6 |
| Vss (L/Kg) | 5.51 |
| Parameters—PO, 10 mg/kg | |
| $T_{max}$ (hr) | 1.00 |
| $C_{max}$ (ng/mL) | 779.58 |
| $AUC_{last}$ (hr*ng/mL) | 3725.56 |
| $AUC_{inf}$ (hr* ng/mL) | 4103.86 |
| F | 74% |

Example B

Oral bioavailability (F)=74%
Clearance=33 mL/min/kg

Example G

The following protocol was used to determine oral bioavailability and clearance, and the results are shown below:
  Species=male mouse;
  Strain=Balb/c;
  18 male mice were divided into two groups Group 1 (3 mg/kg; I.V.), Group 2 (10 mg/kg; P.O.) with each group comprising nine mice;
  Blood samples (approximately 60 μL) were collected from retro orbital plexus under light isoflurane anesthesia such that the samples were obtained at pre-dose, 0.08, 0.25, 0.5, 1, 2, 4, 8 and 24 hr (I.V.) and pre-dose, 0.25, 0.5, 1, 2, 4, 6, 8 and 24 hr (P.O.);

The blood samples were collected from a set of three mice at each time point in labeled micro centrifuge tube containing K2EDTA as anticoagulant;

Plasma samples were separated by centrifugation of whole blood and stored below −70° C. until bioanalysis;

All samples were processed for analysis by protein precipitation using acetonitrile (ACN) and analyzed with fit for purpose LC/MS/MS method (LLOQ: 2.47 ng/mL);

Pharmacokinetic parameters were calculated using the non-compartmental analysis tool of Phoenix WinNonlin (Version 6.3).

Formulation:

Animals in Group 1 were administered intravenously with Example G solution formulation in 5% NMP, 5% solutol HS-15 in 90% HPβCD solution (20% HPβCD in RO water) at 3 mg/kg dose.

Animals in Group 2 were administered orally with 10 mg/kg solution formulation of Example G in 5% NMP, 5% solutol HS-15 in 90% HPβCD solution (20% HPβCD in RO water)

Dosing: 10 mg/kg P.O. and 3 mg/kg I.V.

| Plasma PK Summary: | |
|---|---|
| | Value - Mesylate Salt |
| Parameters - IV, 3 mg/kg | |
| $t_{1/2}$ (hr) | 0.59 |
| $C_{max}$ (ng/mL) | 2205.80 |
| $AUC_{last}$ (hr * ng · mL) | 1918.37 |
| $AUC_{inf}$ (hr * ng/mL) | 1935.24 |
| Clearance (mL/hr/Kg) | 1550.4 |
| Vss (L/Kg) | 1.25 |
| Parameters - PO, 10 mg/kg | |
| $T_{max}$ (hr) | 0.25 |
| $C_{max}$ (ng/mL) | 833.35 |
| $AUC_{last}$ (hr * ng/mL) | 1892.53 |
| $AUC_{inf}$ (hr * ng/mL) | 2144.97 |
| F | 30% |

Example G

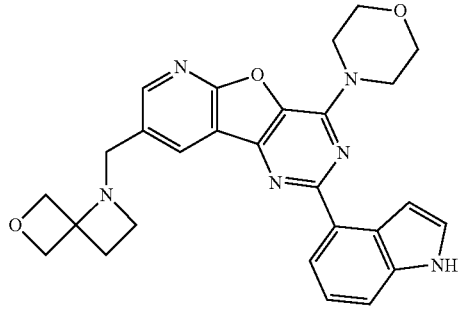 [SMILES: c1cc(-c2nc(N3CCOCC3)c3oc4ncc(CN5CCC56COC6)cc4c3n2)c2cc[nH]c2c1]

Oral bioavailability (F)=30%
Clearance=26 mL/min/kg

Comparative Example (Example I in WO2011/021038)

The following protocol was used to determine oral bioavailability and clearance, and the results are shown below:

Species=male mouse;
Strain=CD1;
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.

Formulation: 10% DMSO, 90% Saline
Dosing: 10 mg/kg P.O. and 5 mg/kg I.V.

| Plasma PK Summary: | | |
|---|---|---|
| | Value - Mesylate Salt | Value - HCl Salt |
| Parameters - IV, 5 mg/kg | | |
| $t_{1/2}$ (hr) | 1.6 | 7.6 |
| $T_{max}$ (hr) | 0.08 | 0.08 |
| $C_{max}$ (ng/mL) | 1618 | 1712 |
| $AUC_{last}$ (hr * ng · mL) | 1245 | 1479 |
| $AUC_{all}$ (hr * ng/mL) | 1245 | 1479 |
| $AUC_{inf}$ (hr * ng/mL) | 1261 | 1515 |
| Clearance (mL/hr/Kg) | 3966 | 3300 |
| Vd (mL/Kg) | 4601 | 10063 |
| Parameters - PO, 10 mg/kg | | |
| $t_{1/2}$ (hr) | 1.9 | 1.8 |
| $T_{max}$ (hr) | 1.0 | 1.0 |
| $C_{max}$ (ng/mL) | 212 | 322 |
| $AUC_{last}$ (hr * ng/mL) | 657 | 849 |
| $AUC_{all}$ (hr * ng/mL) | 657 | 849 |
| $AUC_{inf}$ (hr * ng/mL) | 700 | 896 |
| F | 27.8% | 29.6% |

Example I in WO2011/021038 (Comparative)—mesylate salt form

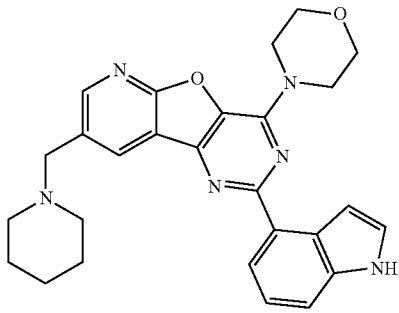 [SMILES: c1cc(-c2nc(N3CCOCC3)c3oc4ncc(CN5CCCCC5)cc4c3n2)c2cc[nH]c2c1]

Oral bioavailability (F)=28%
Clearance=66 mL/min/kg

Summary

| Compound | Oral Bioavailability (F) | Clearance (mL/min/kg) |
|---|---|---|
| Example A | 74 | 21 |
| Example B | 74 | 33 |
| Example G | 30 | 26 |
| Example I from WO2011/021038 (comparative) | 28 | 66 |

Formulation Example

Formulations are examined to provide optimal delivery of API. The different formulations examined are shown in Tables 1 to 7 below. The formulations each contain the API in its succinate salt form. The API used in these formulation studies was the succinate salt form of Example A above. Each formulation that was subjected to dissolution studies was prepared in a solid compressed tablet form. In particular, wet granulated tablet forms were used.

Formulation 7 is identical to Formulation 3, except that it was screened to ensure that a particle size fraction of <500 μm was used. This was done so as to eliminate oversized particles, which may not disintegrate rapidly.

TABLE 1

Formulation 1

| Material | Formula (% w/w) | mg per tablet |
|---|---|---|
| Active Pharmaceutical Ingredient (API) | 25.4 | 190.42 salt (150.0 free base) |
| Lactose monohydrate | 49.6 | 372.08 |
| Microcrystalline cellulose | 15.0 | 112.5 |
| Crospovidone | 5.0 | 37.5 |
| Hydroxypropyl cellulose | 4.0 | 30.0 |
| Magnesium stearate | 1.0 | 7.5 |

TABLE 2

Formulation 2

| Material | Formula (% w/w) | mg per tab |
|---|---|---|
| API | 25.4 | 190.42 salt (150.0 free base) |
| Silicon dioxide | 0.5 | 3.75 |
| Lactose monohydrate | 49.1 | 368.25 |
| Microcrystalline cellulose | 15.0 | 112.5 |
| Crospovidone | 5.0 | 37.5 |
| Hydroxypropyl cellulose | 4.0 | 30.0 |
| Magnesium stearate | 1.0 | 7.5 |

TABLE 3

Formulation 3

| Material | Formula (% w/w) | mg per tab |
|---|---|---|
| API | 25.4 | 190.42 salt (150.0 free base) |
| Sodium lauryl sulfate (SLS) | 0.5 | 3.75 |
| Lactose monohydrate | 49.1 | 368.25 |
| Microcrystalline cellulose | 15 | 112.5 |
| Crospovidone | 5.0 | 37.5 |
| Hydroxypropyl cellulose | 4 | 30.0 |
| Magnesium stearate | 1.0 | 7.5 |

TABLE 4

Formulation 4

| Material | Formula (% w/w) | mg per tab |
|---|---|---|
| API | 25.4 | 190.42 salt (150.0 free base) |
| Hydroxypropyl-beta-cyclodextrin (HPBCD) | 20.0 | 150.0 |
| Lactose monohydrate | 29.6 | 222.08 |
| Microcrystalline cellulose | 15.0 | 112.5 |
| Crospovidone | 5.0 | 37.5 |
| Hydroxypropyl cellulose | 4.0 | 30.0 |
| Magnesium stearate | 1.0 | 7.5 |

TABLE 5

Formulation 6

| Material | Formula (% w/w) | mg per tab |
|---|---|---|
| API | 25.4 | 190.42 salt (150.0 free base) |
| Sodium lauryl sulfate (SLS) | 1.0 | 7.5 |
| Lactose monohydrate | 48.6 | 364.58 |
| Microcrystalline cellulose | 15.0 | 112.5 |
| Crospovidone | 5.0 | 37.5 |
| Hydroxypropyl cellulose | 4.0 | 30.0 |
| Magnesium stearate | 1.0 | 7.5 |

TABLE 6

Formulation 7

| Material | Formula (% w/w) | mg per tab |
|---|---|---|
| API | 25.4 | 190.42 salt (150.0 free base) |
| Sodium lauryl sulfate (SLS) | 0.5 | 3.75 |
| Lactose monohydrate | 49.1 | 368.25 |
| Microcrystalline cellulose | 15 | 112.5 |
| Crospovidone | 5.0 | 37.5 |
| Hydroxypropyl cellulose | 4 | 30.0 |
| Magnesium stearate | 1.0 | 7.5 |

TABLE 7

Formulation 8

| Material | Formula (% w/w) | mg per tab |
|---|---|---|
| API | 25.4 | 190.42 salt (150.0 free base) |
| Sodium lauryl sulfate (SLS) | 0.5 | 3.75 |
| Lactose monohydrate | 47.6 | 357.00 |
| Microcrystalline cellulose | 15.0 | 112.5 |
| Crospovidone XL10 | 6.5 | 48.75 |
| Hydroxypropyl cellulose | 4.0 | 30.0 |
| Magnesium stearate | 1.0 | 7.5 |

The equipment used in these studies is shown in Table 8 below:

TABLE 8

Equipment used for manufacturing and testing succinate salt tablets

| Equipment name | Function |
|---|---|
| Balances | Weighing |
| Timer | Timing |
| Turbula Blender | Mixing |
| Kenwood Mini-chopper | Granulation |
| Oven | Drying |
| Moisture balance | Loss on drying |
| Sieves 1000 and 250 μm | Screening materials |
| Syringe | Addition of water |
| Manesty F-press | Compression |
| 12 mm Normal Round Concave (nrc) tooling | Compression |
| Disintegration batch | Disintegration |
| Dissolution apparatus (paddles) | Dissolution |
| Tap Density Meter | Density determination of blend |

Formulations 1 to 4 were produced and tested first. A summary of the manufacture is provided below in Table 9.

TABLE 9

Process Data for Formulations 1 to 4

| Formulation | 1 | 2 | 3 | 4 |
|---|---|---|---|---|
| Initial LOD (%) | 2.30 | Same as Formulation 1 | Same as Formulation 1 | Same as Formulation 1 |
| Amount of water added (ml) | 10 | 7.5 | 7.5 | 5 |
| Granulation comments | Agglomerates viable | Granulation appears sufficient | Satisfactory granules some lumps | Granulation looks complete |
| Drying time (hours) | 4 | 2 | 1 hour 50 minutes | 3 |
| Final LOD (%) | 2.17 | 1.84 | 1.87 | 1.19 |
| Yield (%) | 94 | 92.2 | 96.5 | 90 |
| Weight >1 mm (mild shaking) (g) | 12.43 | 9.01 | 8.18 | 6.25 |
| Weight >1 mm (post screening) (g) | 0.26 | 0.09 | 0.01 | 0.60 |
| Press setting to achieve hardness (no units) | 32 | 39 | 39 | Not recorded |
| Average hardness (kP) | 13.8 | 13.2 | 13.5 | Not recorded |
| Disintegration time minimum (min:sec) | 1:38 | 1:01 | 2:12 | >15 mins |
| Disintegration time maximum (min:sec) | 6:30 | 15:48 Note $5^{th}$ tablet disintegrated in 5:05 | 7:09 | >15 mins |

Good granules were produced for all formulations. Formulation 4 required much less water than the other batches, most likely because of the presence of HPBCD. All formulations produced free flowing granules that compressed well into 12 mm nrc (Normal Round Concave) tablets with no picking or sticking.

Disintegration for three out of four of these batches was within the 15 minute specification. Formulation 1 was the fastest although it was noted that relatively large granules were produced from the breakup of the tablet. Formulation 4 did not disintegrate well and was not studied further. This is surprising given the high aqueous solubility of HPBCD. Dissolution was performed in 450 ml fasted state simulated gastric fluid (FaSSGF) at pH 1.6 with a stirring speed of 75 rpm (USP apparatus II). The mean dissolution results for the 3 formulations tested versus a suspension formulation (2% Methocel, 100 mg/ml (as free base), 1.5 ml) (Formulation 5) are given in Table 10.

TABLE 10

Mean dissolution data for Formulations 1 to 3, and 5

| Formulation | 5 min | 10 min | 15 min | 30 min |
|---|---|---|---|---|
| 5 | 95 | 96 | 96 | 96 |
| 1 | 59 | 65 | 67 | 70 |
| 2 | 25 | 28 | 31 | 35 |
| 3 | 68 | 72 | 73 | 78 |

The data for formulations 1 and 3 show good dissolution but are not as good as the preclinical suspension formulation which provides good exposure in preclinical toxicology species. It was thought this may be due to the large granule size noted in the disintegration. Other strategies to improve dissolution were attempted in the next set of experiments. In an attempt to increase the dissolution from 80 to 90-100% the following options were looked at based on Formulation 3, as this showed the most promising results:

Formulation 6: Increase the amount of SLS in the formulation from 0.5% to 1%.

Formulation 7: Manufacture a batch based on Formulation 3 and screen to ensure a particle size fraction of <500 μm is used. This is to eliminate oversize particles which may not dissolve rapidly.

Formulation 8: Increase the amount of intra-granular disintegrant from 2.5% to 4% and change grade to Crospovidone XL-10. This is a finer grade of disintegrant with a larger surface area. Extra-granular disintegrant was not increased as the tablet disintegration time was sufficient.

These batches were manufactured as before, except that the tablets were pressed manually on an F3 press, but to the same target hardness and weight. The process data is given in Table 11.

TABLE 11

Process Data for Formulations 7 to 9

| Formulation | 6 | 7 | 8 |
|---|---|---|---|
| Initial LOD (%) | Same as Formulation 1 | Same as Formulation 1 | Same as Formulation 1 |
| Amount of water added (ml) | 7.5 | 7.5 | 8.5 |
| Granulation comments | Good granules | Good granules | Granulated |
| Drying time (hours) | 3 | 3 | 3 |
| Final LOD (%) | 1.52 | 1.75 | 2.18 |
| Yield (%) | 95.3 | 97.2 | 96.9 |
| Weight >1 mm (mild shaking) (g) | 6.47 | 7.56 | 4.95 |
| Weight >1 mm (post screening) (g) | 0.36 | 0.04 | 0.01 |
| Press setting to achieve hardness (no units) | 35 | 32 | 37 |
| Average hardness (kP) | 9.8 | 10.1 | 12.7 |
| Disintegration time minimum (min:sec) | 1:39 | 1:20 | 3:56 |
| Disintegration time maximum (min:sec) | 4:48 | 1:54 | 8:43 |

Formulation 7 granules were screened post lubrication so that only granules having a particle size of <500 μm were used. The yield of these granules was 92.5% indicating good granulation control.

Good granules were produced for all formulations. All formulations used less granulating fluid compared to the initial experiments as a lighter granulation end point was thought desirable.

The disintegration times were all rapid with Formulation 7 very fast.

The mean dissolution data (FaSSGF) is given in Table 12. The data show that 100% release can be achieved from a tablet formulation of a compound according for formula I (specifically the succinate salt form of Example A above). Surprisingly the additional and finer disintegrant did not show such an effect, but the formulations with fine particles and additional surfactant do perform well in this dissolution test. Formulation 7 performs the best in disintegration and dissolution, but there is a potential for a decreased yield. Hence, formulation 6 was selected as the lead formulation because it gave suitable dissolution and did not require the additional screening process step and potential loss of yield compared to formulation 7.

TABLE 12

Mean dissolution data for Formulation 6 to 8

| Formulation | 5 min | 10 min | 15 min | 30 min |
|---|---|---|---|---|
| 6 | 88 | 94 | 95 | 96 |
| 7 | 89 | 98 | 99 | 100 |
| 8 | 69 | 72 | 74 | 83 |

Details Relating to the Manufacturing Process and Process Controls for Batch Quantity FIG. 1 is a flow chart illustrating the process used for preparing a batch quantity of 1.2 kg of Example A in tablet form.

The intra-granular excipients and Example A were sieved using a 1000 μm screen directly into a 6 L granulation bowl. The blend was mixed for 2 minutes at 200 rpm and the initial loss on drying (LOD) recorded using an Infra-Red (IR) moisture balance set at 105° C.

The binder fluid was prepared by dissolving sodium lauryl sulfate (SLS) in water using a magnetic stirrer mixing gently to minimise aeration. Water is sampled for conductivity and microbiological testing.

The mixer was set with an impeller speed of 75 rpm and a chopper speed of 500 rpm. The SLS solution was sprayed onto the powder bed at a target addition speed of 20 g per minute using a previously calibrated peristaltic pump. The appearance of the granules was noted. If the appearance of the granules was not suitable (under-granulated or dusty), up to an additional 1 minute of mixing was permitted. The additional mixing time and final appearance are recorded.

The granules were transferred to the fluid bed dryer. The inlet temperature was set to 60±5° C. and the granules dried using the minimum airflow required to fluidise the bed. The temperature was adjusted manually as required to stay within the temperature set point range. The drying parameters were recorded initially and then every 10 minutes.

A 5 g representative sample was taken after 20 minutes and the moisture content determined using an LOD IR moisture balance set at 105° C. The moisture content should be within 0.5% w/w of the initial value. If drying is incomplete and the target moisture content is not achieved, continue drying until the target moisture content is achieved.

The granules were transferred into a clean plastic bag and the gross and net weight calculated.

The granules were milled using a conical mill with 813 μm screen. The net weight of any material that does not pass through the screen is recorded and rejected.

The milled granules were transferred into a clean, labelled 10 or 20 L blender vessel.

The remaining crospovidone (extra-granular component), adjusted for the dry granule yield, was sieved using a 1000 μm screen, transferred to the 10 or 20 L blender shell and mixed for 16 minutes at 20±2 rpm. The blending time, speed and net weight of contents are recorded.

The magnesium stearate, adjusted for the dry granule yield, was co-screened with an equal or greater than equal portion of the blend through a 500 μm mesh into the 10 or 20 L blending shell and mixed for 1 minute at 30±2 rpm. The blending time, speed and net weight of contents were recorded.

The blend was tested for bulk and tapped densities.

The Riva Piccola (or equivalent) tablet press was set up as follows for the different size of tablet required:

For 750 mg caplets (containing 150 mg of Example A free base): the tablet press is set up using 16.0×8.0 mm capsule shaped tooling. The granules are compressed on the compression machine to a bulk hardness of 16 kP.

For 500 mg caplets (containing 100 mg of Example A free base): the tablet press is set up using 14.0×7.0 mm capsule shaped tooling. The granules are compressed on the compression machine to a bulk hardness of 15.5 kP.

For 250 mg caplets (containing 50 mg of Example A free base): the tablet press is set up using 12.0×6.0 mm capsule shaped tooling. The granules are compressed on the compression machine to a bulk hardness of 13 kP.

Compressed tablets are de-dusted and passed through a metal detector prior to bulk packaging. Early drug substance stability data, binary mix compatibility data and a 4 week pre-formulation study on qualitatively similar tablets demonstrated that the tablets are chemically stable.

Samples were taken for in-process testing, as described below, and the total time taken for the run recorded. The tablets were assessed as follows:

| In-process test | Specification | | | | | Testing frequency |
|---|---|---|---|---|---|---|
| Appearance | Free from chips, cracks, picking, pitting and surface spots | | | | | 20 tablets at start up and every 15 minutes during run |
| Thickness (mm) | For information only | | | | | 10 tablets at start up and every 30 minutes during run |
| Tablet hardness (Ph. Eur 2.9.8) | Targets (kP): 150 mg – 16 ± 2 100 mg – 15.5 ± 2 50 mg – 13 ± 2 | | | | | 10 tablets at start up and every 30 minutes during run |
| Friability (Ph. Eur. 2.9.7) | Test time: 4 minutes Limit: <0.3% | | | | | 6.5 g of tablets at start up and end of run (each day) |
| Disintegration (Ph. Eur. 2.9.1) in water | Not more than 15 minutes | | | | | 6 tablets at start, middle and end of run (each day) |
| Weight | Action limits | | Warning limits | | | 20 tablets at start up |
| uniformity, Mean weight (Ph. Eur. 2.9.5) | Target 750 500 250 | –5% 712.50 475.00 237.50 | +5% 787.50 525.00 262.50 | –3.5% 723.75 482.50 241.25 | +3.5% 776.25 517.50 258.75 | and every 15 minutes of compression run |
| Weight | Action limits | | Warning limits | | | 20 tablets at start up |
| uniformity, Individual weights (Ph. Eur. 2.9.5) | Target 750 500 250 | –7.5% 693.75 462.50 231.25 | +7.5% 806.25 537.50 268.50 | –5% 712.50 475.00 237.50 | +5% 787.50 525.00 262.50 | and every 15 minutes of compression run |

Conclusions

These formulation studies show that disintegration and particle size are important for achieving dissolution of a compound according to formula I (specifically the succinate salt form of Example A above). In addition, it may be the case that wetting is also important.

The invention claimed is:

1. A pharmaceutical composition comprising a succinate salt of a compound, wherein the compound is represented by:

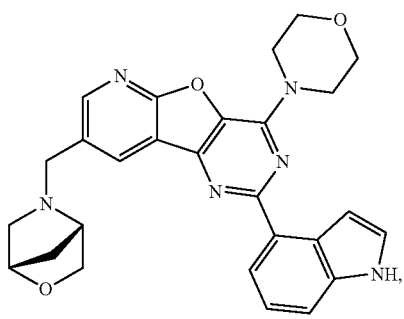 [SMILES: c1cc(-c2nc(N3CCOCC3)c3oc4ncc(CN5C[C@@H]6C[C@H]5CO6)cc4c3n2)c2cc[nH]c2c1]

and at least one pharmaceutical excipient selected from the group consisting of fillers, binders, disintegrants, glidants and lubricants.

2. The composition according to claim 1, further comprising a surfactant in an amount of from 0.1 to 5 wt % based on the total weight of the composition.

3. The composition according to claim 1, wherein the composition is in the form of a tablet or capsule.

4. The composition according to claim 1, wherein the composition comprises at least two pharmaceutical excipients.

5. The composition according to claim 1, wherein the compound is present in an amount of from 5 to 30 wt % based on the total weight of the composition.

6. The composition according to claim 1, wherein a filler is present in an amount of from 10 to 90 wt % based on the total weight of the composition.

7. The composition according to claim 1, wherein a binder is present in an amount of from 0.1 to 20 wt % based on the total weight of the composition.

8. The composition according to claim 1, wherein a disintegrant is present in an amount of from 1 to 20 wt % based on the total weight of the composition.

9. The composition according to claim 1, wherein a lubricant is present in an amount of from 0.1 to 10 wt % based on the total weight of the composition.

10. The composition according to claim 1, wherein the composition comprises:
   1 to 50 wt % of a compound according to claim 1;
   10 to 90 wt % of at least one filler;
   0.1 to 20 wt % of at least one binder;
   1 to 20 wt % of at least one disintegrant; and
   0.1 to 10 wt % of at least one lubricant or glidant.

11. The pharmaceutical composition of claim 1, wherein the pharmaceutical excipient is selected from the group consisting of lactose monohydrate, microcrystalline cellulose, crospovidone, hydroxypropyl cellulose, magnesium stearate, and sodium lauryl sulfate.

12. The pharmaceutical composition of claim 1, wherein the composition comprises sodium lauryl sulfate, lactose monohydrate, microcrystalline cellulose, crospovidone, hydroxypropyl cellulose, and magnesium stearate.

* * * * *